(12) United States Patent
Xiong et al.

(10) Patent No.: US 7,995,832 B2
(45) Date of Patent: Aug. 9, 2011

(54) PHOTOMASK INSPECTION AND VERIFICATION BY LITHOGRAPHY IMAGE RECONSTRUCTION USING IMAGING PUPIL FILTERS

(75) Inventors: Yalin Xiong, Union City, CA (US);
Rui-Fang Shi, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1227 days.

(21) Appl. No.: 11/669,014

(22) Filed: Jan. 30, 2007

(65) Prior Publication Data

US 2008/0170774 A1 Jul. 17, 2008

Related U.S. Application Data

(60) Provisional application No. 60/884,601, filed on Jan. 11, 2007.

(51) Int. Cl.
*G06K 9/00* (2006.01)
(52) U.S. Cl. .......................................... 382/144; 382/260
(58) Field of Classification Search ........... 382/144–145
See application file for complete search history.

(56) References Cited

U.S. PATENT DOCUMENTS

| | | | | |
|---|---|---|---|---|
| 5,537,260 A * | 7/1996 | Williamson | ...... | 359/727 |
| 5,559,583 A * | 9/1996 | Tanabe | ...... | 355/71 |
| 5,838,433 A * | 11/1998 | Hagiwara | ...... | 356/364 |
| 5,960,106 A * | 9/1999 | Tsuchiya et al. | ...... | 382/144 |
| 7,133,119 B1 * | 11/2006 | Pettibone et al. | ...... | 355/71 |
| 7,535,640 B2 * | 5/2009 | Totzeck et al. | ...... | 359/486.01 |
| 7,545,510 B2 * | 6/2009 | Lee et al. | ...... | 356/503 |
| 2003/0128349 A1 * | 7/2003 | Unno | ...... | 355/67 |
| 2003/0179919 A1 * | 9/2003 | Goldberg et al. | ...... | 382/141 |
| 2003/0226951 A1 * | 12/2003 | Ye et al. | ...... | 250/208.1 |
| 2004/0016897 A1 * | 1/2004 | Stokowski et al. | ...... | 250/559.45 |
| 2005/0046863 A1 * | 3/2005 | Millerd et al. | ...... | 356/495 |
| 2005/0097500 A1 * | 5/2005 | Ye et al. | ...... | 716/20 |
| 2005/0270608 A1 * | 12/2005 | Shiozawa et al. | ...... | 359/15 |
| 2006/0007541 A1 | 1/2006 | Totzeck et al. | | |
| 2006/0012873 A1 * | 1/2006 | Totzeck et al. | ...... | 359/386 |
| 2006/0275708 A1 * | 12/2006 | Baba-Ali et al. | ...... | 430/311 |

OTHER PUBLICATIONS

Pupil-plane—technique, J.K.Boger, 0146-9592, 1999, Optics letters, vol. 24, No. 9, pp. 611-613.*
XP-002496441, Bisschop et al., SPIE, 2007, vol. 6730, pp. 1-12.*
XP-002496392, Zibold et al., SPIE, vol. 6283, 2006, pp. 1-8.*
High-numerical aperture—in photoresist, Flagello et al., 0003-6935, 1997, Applied optics vol. 36 No. 34, pp. 8944-8951.*

(Continued)

*Primary Examiner* — Samir A Ahmed
*Assistant Examiner* — Jayesh Patel
(74) *Attorney, Agent, or Firm* — Suiter Swantz pc llo

(57) ABSTRACT

A method and tool for generating reconstructed images that model the high NA effects of a lithography tool used to image patterns produced by a mask. Comparison of the reconstructed images with reference images characterize the mask. The method involves providing a mask reticle for inspection. Generating matrix values associated with a high NA corrective filter matrix that characterizes a high NA lithography system used to print from the mask. Illuminating the mask to produce a patterned illumination beam that is filtered with filters associated with the high NA corrective filter matrix elements to obtain a plurality of filtered beams that include raw image data that is processed to obtain a reconstructed image that is further processed and compared with reference images to obtain mask characterization information.

18 Claims, 11 Drawing Sheets

OTHER PUBLICATIONS

Zibold A et al: "First results for hyper NA scanner emulation from AIMS(TM) 45-193I" Proceedings of the SPIE—The International Society for Optical Engineering SPIE—Int. Soc. Opt. Eng USA, vol. 6283, No. 1, Apr. 18, 2006, pp. 628312-1, XP002496392 ISSN: 0277-786X.

Database Compendex [Online]Engineering Information, Inc., New York, NY, US; Sep. 18, 2007, De Bisschop P et al: "Using the AIMS (TM) 45-193I f o r hyper-NA imaging applications" XP002496393 Database accession No. E20081711216727.

De Bisschop P et al.: "Using the AIMSCTM) 45-193i for hyper-NA imaging applications" Proceedings of SPIE—The International Society for Optical Engineering—Photomask Technology 2007 2007 SPIE US,vol. 6730, Sep. 18, 2007, pp. 1-12, P002496441.

International Search Report from PCT/US2008/050798, mailed Oct. 9, 2008.

Written Opinion from PCT/US2008/050798, mailed Oct. 9, 2008.

\* cited by examiner

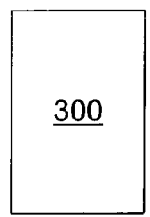 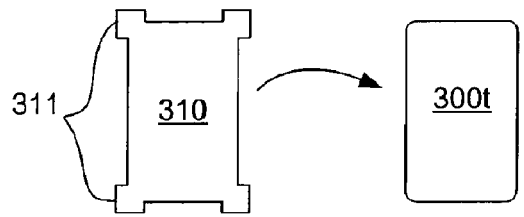
FIG. 3(a)   FIG. 3(b)   FIG. 3(c)
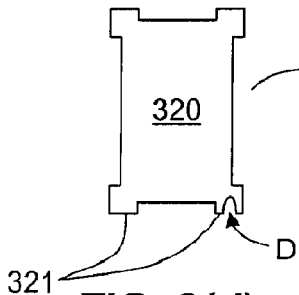 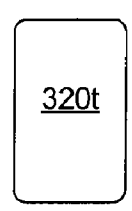 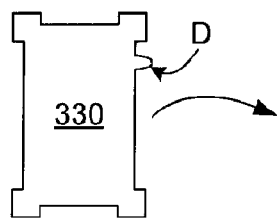 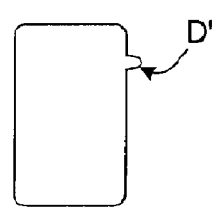
FIG. 3(d)   FIG. 3(e)   FIG. 3(f)   FIG. 3(g)
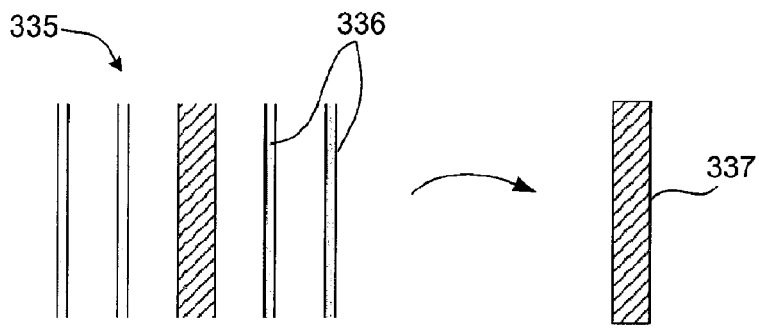
FIG. 3(h)
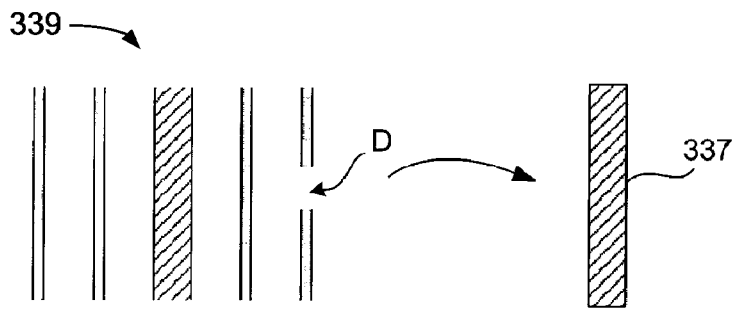
FIG. 3(i)

Mxy  Mxz

PHOTOMASK INSPECTION AND VERIFICATION BY LITHOGRAPHY IMAGE RECONSTRUCTION USING IMAGING PUPIL FILTERS

RELATED APPLICATION

This application claims priority to U.S. Provisional Application No. 60/884,601 filed Jan. 11, 2007, which application is hereby incorporated by reference.

TECHNICAL FIELD

The invention described herein relates generally to photomask pattern inspection and verification techniques. In particular, the invention relates to systems and methods for synthesizing accurate lithographic images (i.e. images formed with production tools such as steppers, scanners, and the like) using conventional high-speed optical microscopes having modified optics and specialized process instructions adaptable for use in many applications including, but not limited to, photomask inspection, photomask AIMS review, and photomask verification.

BACKGROUND

A serious problem exists in the photolithographic arts. Surprisingly enough, this problem is that the existing high-resolution optical inspection systems (i.e. optical microscope) can detect almost every defect on a wafer. This is problematic because it is not always necessary to detect all defects on an inspection surface at all times. For example, during a photomask fabrication process, the ability to detect all defects is important, but the same may not be true always true during associated wafer production processes. Still worse, the present art has no efficient method of separating the unimportant defects from the lithographically significant defects. Currently, it requires massive amounts of time and effort to separate the important and unimportant defects. The inventors have developed methods and apparatus for vastly reducing this time and for more efficiently sorting out the lithographically significant defects.

Integrated circuit fabrication utilizes photolithographic processes which use photomasks or reticles and a projection optical system (e.g. stepper or scanner) to project circuit images onto silicon wafers. A high production yield is contingent on having defect-free masks and reticles. Since it is inevitable that defects will occur in the mask, these defects must be found and repaired prior to using the mask.

Automated mask inspection systems have existed for over 20 years. The earliest such system, the Bell Telephone Laboratories AMIS system (John Bruning et al., "An Automated Mask Inspection System—AMIS", IEEE Transactions on Electron Devices, Vol. ED-22, No. 7 July 1971, pp 487 to 495), used a laser that scanned the mask. Subsequent systems used a linear sensor to inspect an image projected by the mask, such as described by Levy et al. (U.S. Pat. No. 4,247,203, "Automatic Photomask Inspection System and Apparatus"). Such a technology teaches die-to-die inspection, i.e., inspection of two adjacent dice by comparing them to each other.

As the complexity of integrated circuits has increased and the size of features has decreased, so have the demands on the manufacturing and inspection processes. Many tools and approaches have been developed to address this need for accurate defect detection. Commonly, mask inspection is performed using high resolution magnifying optical inspection systems. Such systems use high magnification optical systems to project mask reticle images onto sensors to enable defect detection and analysis. These devices have high numerical aperture (NA) in the imaging plane. These devices have become so effective at detecting defects that mask inspections can reveal thousands of defects on a single mask. Unfortunately, this requires that each defect be individually examined to gauge its lithographic significance in the final printed pattern. Needless to say this can take a very long time and using current technologies and defect modeling is a very error prone process. Consequently, such inspections generate a significant process bottleneck.

FIG. 1A provides a simplified schematic depiction of an existing photolithographic patterning apparatus 100. One example is a stepper apparatus configured to conduct pattern transfer between a mask reticle to a substrate (commonly, a photoresist layer on the substrate). Commonly, an illumination source 101 directs a light beam into the illumination optics 102 of the stepper 100. The illumination optics 102 here are represented by the extremely simplified depiction of FIG. 1(a). The illumination optic system 102 can include, for example, collimating optics 102a, an aperture 102b, and focusing optics 102c all integrated to form an illumination beam 103 that is directed onto a selected portion of a mask reticle M. The mask, of course, affects the beam to form a patterning beam 104 that is directed into projection optics 105 which focuses the beam onto a selected location of a target 106. For such a reduction optical system, the ratio between the image NA (numerical aperture) at 105i and the object NA at 105o is a reduction factor (for example, a 4× reduction factor is common). It is pointed out, that in order to achieve high-resolution pattern transfer and 4× reduction in size, projection systems employ projection optics 105 having a high image NA 105i and a low object NA 105o. For the purposes of this disclosure, a high NA generally has a value greater than 0.85 and more particularly greater than about 1.0. Thus, in the system of FIG. 1 the high image NA 105i has an NA of about 0.85 or greater. These NA's can also be enhanced using immersion fluids. In contrast, the object NA 105o on the same systems are generally above 0.20. For example, to achieve a 4× magnification on a system with an image NA 105i of about 0.85, an objective NA of about 0.2125 ($^{0.85}/4$) is used. Similarly, for a system with an image NA of about 1.00 an objective NA of about 0.25 can be employed.

However, when inspections are performed, systems having different optical parameters are employed. Detectors (CCD's and the like) are commonly formed with pixel sizes in the 10 micron range. Thus high magnifications are required so that the detectors can image the very small sub-micron features of the mask. For example, inspection tools commonly have a relatively high object NA coupled with a low image NA in order to obtain the required degree of magnification. Additionally, because mask features are continually decreasing in size (in the range of 10's of nanometers) increasing magnifications are required. Thus, magnifications on the order of 200× or more (and higher) are often used to conduct inspections.

FIG. 1B illustrates an example prior art inspection tool 200 showing the need for high magnification optics 207 having small image NA's 107i. An illumination source 201 directs a light beam into the illumination optics 202 of the inspection tool 200. The illumination optics 202 here are represented in an extremely simplified depiction in FIG. 1B. The illumination optic system 202 can include, for example, collimating optics 202a, an aperture 202b, and focusing optics 202c all integrated to form an illumination beam 203 that is directed onto a selected portion of a mask reticle M. The parameters of the illumination optical system 202 are subject to a wide range of variability. The mask M, of course, affects the beam to form an inspection pattern beam 204 that is directed into magnifying optics 207 which focuses the beam onto a detector element 208 where it produces a signal corresponding to the received light. It is pointed out, that for achieving high magnification, generally a high object NA at 107o and low image NA at 107i are employed. Typically, a high object NA for an inspection tool is in the range of about 0.5-0.9, and the corresponding low image NAs are below 0.01. Such lens systems give suitable magnification.

Such mask inspection and defect detection tools are very efficient at locating defects. Given the current state of technology an inspection can reveal the number of defects in the range of hundreds to thousands or more per mask. During a photomask fabrication and inspection process, finding all those defects is generally considered desirable and beneficial. However, during wafer production processes, it is sometimes desirable to detect only those defects that have a lithographically significant impact on the actual photolithographic pattern. Unfortunately, current technologies require that each defect be individually examined to gauge its effect of the photolithographic pattern. Worse still, examining each of the thousands of defects is so time-consuming as to be prohibitive. This is doubly troublesome because many defects discovered are relatively unimportant and have little or no effect of the pattern as printed. Regrettably, given the current state of the art, it is difficult, if not impossible to determine if a given defect is important or not. So, currently all defects must be subject secondary inspection and verification of their significance.

It would be advantageous if an inspection could determine whether a given defect is lithographically significant before any such further inspection is performed. By lithographically significant the inventors mean that a defect has lithographic significance in the final printed pattern. That is to say, that some defects, although present in the mask, have no significant impact on the printed pattern transferred to a photoresist layer of a substrate. For example, in some cases the defect can be so small (or on a lithographically insensitive portion of the pattern) as to be largely irrelevant. Another particularly troublesome family defect sites that are difficult to characterize are defects in so-called assist or OPC features. This problem is becoming particularly common with the increased reliance on RET (Resolution Enhancement Techniques) masks. Such masks commonly contain optical proximity correction (OPC) features and SRAFs (Sub-Resolution Assist Features). Such features although important for purposes of obtaining accurate feature representation on the final wafer may not be affected by the presence of small defects.

Thus, a lithographically significant defect is a defect that is present on the mask, but more importantly, its presence on the mask reticle can cause an effect in the lithographically transferred pattern. Such lithographically significant defects can cause problems related to circuit failures, sub optimal performance, and so on.

FIGS. 3(a)-3(i) schematically illustrate some aspects of lithographically significant defects.

FIG. 3(a) depicts, for example, the rectangular shape of an intended feature 300 that a designer wishes to print onto target surface (usually a photoresist). At small dimensions standard binary masks frequently don't do a very good job of achieving accurate photolithographic pattern transfer. However, in many cases OPC features can be used to enhance pattern transfer fidelity. FIG. 3(b) is a schematic simplified depiction of a mask pattern feature 310 that can be used to print an improved pattern onto the substrate. For example, in some pattern embodiments, OPC features 311 can be added to the corners to increase pattern transfer fidelity. FIG. 3(c) illustrates pattern 300t produced by photolithographic transfer onto the substrate. It is noted that the corners are a little rounded, but the pattern is generally very close to the design specification 300. Typically, design patterns are not expected to be perfect, but rather to conform to some pre-specified tolerance or optical design rule (ODR) specified by the designer or manufacturer. A feature in compliance with the ODR is satisfactory and not deemed to have defects. For the illustrative purposes of this patent, this transferred (or printed) feature 300t is considered to have no defects.

FIG. 3(d) depicts a mask pattern 320 similar to that of FIG. 3(b). The important difference being that there is a defect D in the mask pattern. Significantly, the inventors point out that the defect D is in one of the OPC features 321. The question is whether the defect is bad enough to have any photolithographic consequences when printed to the substrate. For the sake of this patent, in this illustration, the defects small size and presence in an OPC feature have prevented it from being printed to the substrate (See, FIG. 3(e) which shows the resultant printed feature 320t having no evidence of the defect). This defect is not generally significant and generally presents a costly waste of time to classify or repair. This defect is presented in contrast with the defect in FIG. 3(f). FIG. 3(f) depicts a mask pattern 330 generally similar to that of FIG. 3(b) with the exception being that there is a defect D in the mask pattern. Significantly, this defect is not in an OPC area and is in (for example) an optically sensitive region of the mask pattern. If the defect is large enough it will present a defect artifact when it is printed onto the substrate. FIG. 3(g) illustrates the problem when the defect D prints to the substrate. Here an observable artifact D" of the defect D is printed. This defect is said to be photolithographically significant because it produces observable consequences when printed to the substrate.

This issue comes to rise in many situations in photolithographic processing. For example, in line printing a line feature can include several "assist" or SRAF features to enable the line to be printed robustly within process window. This phenomenon is briefly illustrated in figurative illustrations FIG. 3(h) and FIG. 3(i). FIG. 3(h) shows a mask pattern 335 used to generate a line 337 when printed onto a substrate surface. Notable are the presence of assist features 336 which do not print onto the substrate. FIG. 3(i) gives one example of a lithographically insignificant defect D. FIG. 3(i) shows a defect bearing mask pattern 339 used to generate a line when printed onto a substrate surface. In this case, the presence of defect D does not affect the final line 337 as printed. Thus, the difference between lithographically significant defects and less important defects is generally understood. The inventors point out that these examples are illustrations only and the invention, as disclosed herein, is not to be limited by such examples.

The schematic depictions of the images such as shown in FIGS. 3(c), 3(e), 3(g), and the right hand portions of FIGS. 3(h) and 3(i) are how a high NA lithographic system "sees" or reproduces and image. None of the OPC features are printed. As such, these OPC features, although present in the mask and necessary to obtain satisfactory pattern fidelity, are lithographically insignificant. High magnification tools see the OPC features just as if they were the pattern itself.

Others have attempted photomask inspection based on photolithographic significance. However, such systems have encountered a number of problems. FIG. 2 is an illustration of a common prior art inspection system 210 embodied in some prior art approaches. In such prior art systems and techniques, the optical characteristics of the illumination optics 211 are modeled on those of the stepper systems used. Additionally, the object NA 212o of the inspection system 210 is matched to a corresponding stepper in order to mimic the stepper optically. But, such optical parameters are not sufficient to provide the required magnification to enable inspection. Accordingly, a magnification optical system 213 must be employed on the imaging side in order to image the photomask onto sensors 214. Because the stepper systems all use a relatively low object NA 212o and even lower NA is required on the imaging side. Thus, the image NA 212i of optical system 213 has a very small NA. However, as a result of the changes to the optical properties of such systems, these magnification systems do not accurately model the lithographic properties of the high NA (image NA) systems (e.g., FIG. 1A) used to form patterns of the desired surfaces. Accordingly, the accuracy of measurements of photolithographic significance has been distorted by the changes in the optical system to such a degree as to be insufficient for the state-of-art lithography pattern defect detection. Thus their usefulness in photomask inspection has been severely limited. The current invention is intended to address the shortcomings of the prior by introducing new methods and apparatus approaches.

The inventors note that similar problems exist in photomask AIMS (Aerial Image Measurements Systems) review. As is known to those having ordinary skill in the art, photomask AIMS review stations are typically used to examine individual sites (i.e., individual defects or repairs done on a defect) to gauge the effect the inspected site will have on the transferred wafer pattern. Prior art photomask AIMS review systems also match the object NA of the review tool to that of the corresponding stepper used to transfer the associated pattern. Similarly, very low image NA's are used to achieved the required magnification. Not surprisingly, the prediction accuracy of such systems is unsatisfactory as the state-of-art photolithography patterning uses a higher image NA (further enhanced with an immersion liquid) than is used for the AIMS review tool. Thus improvements are need for these tools as well.

Additionally, the invention as disclosed herein present opportunities for improving wafer pattern verification techniques. Such verification is used to confirm that wafer patterns resulted from photolithographic processes produce the patterns that the designers wanted originally. Currently, the state-of-art verification technique is to perform verification on post-OPC design layout or e-beam wafer verification. In one prior art approach, a perfect design layout is used to simulate what the wafer pattern would be. The drawback of this approach is that it cannot take compensate for imperfect mask fabrication which is present in almost all cases. Accordingly, there are systematic differences between the pattern drawn in those layouts versus what is actually on the mask. Another approach uses e-beam imaging to acquire high-resolution e-beam images of the wafer pattern itself. Some drawbacks of this approach include the low speed at which such e-beam imaging is performed and the high signal-to-noise ratio for this method. In accordance with some embodiments of the invention, accurate photolithographic images acquired using the present inventive reticle inspection system can be used to predict accurately the wafer pattern, thus enabling a full-chip high-speed verification against the intended wafer pattern. Thus, the present invention offers room for improvement in the pattern verification domain as well.

The embodiments of invention present substantial advances over the existing methodologies and overcome many limitations of the existing art in photomask inspection, AIMS review and verification. These and other inventive aspects of the invention will be discussed herein below.

SUMMARY OF THE INVENTION

In accordance with the principles of the present invention, tools and methodologies for generating reconstructed images and identifying lithographically significant defects are disclosed.

Numerous aspects of the present invention are described in detail in the following description and drawings set forth hereinbelow.

In one embodiment, the invention teaches a method for generating a reconstructed image and identifying lithographically significant defects. The method involves inspecting a mask reticle configured for photolithographic transfer of a mask pattern onto a substrate using a high image numeric aperture (NA) lithography system. The method involves obtaining high NA correction filters suitable for correcting image data obtained using a low NA high magnification inspection system to model high image NA effects of a lithography ordinarily used to pattern wafers and other imageable surfaces. The mask is inspected by illumination to produce a patterned beam. The patterned beam is filtered with a plurality of high NA correction filters to obtain a plurality of filtered beams. The filtered beams are captured to generate raw image data associated with each filtered beam. The raw image data is processed to obtain a reconstructed image which simulates an image as projected by the mask reticle using a lithography system. The reconstructed images can be processed and compared with suitable reference or baseline images to obtain mask characterization information. This process can be used to facilitate defect detection and pattern verification for the mask reticle.

In one embodiment, the invention teaches apparatus for inspecting and characterizing mask reticles. The apparatus includes an illumination system that illuminates a mask reticle to produce a patterned beam. Magnification optics are positioned to receive the patterned illumination beam and magnify and project the beam onto an image sensor. The magnification optics include a filter arranged in the pupil plane (of the magnification optics) to model optical effects produced by a lithographic device used to print image patterns from the mask reticle. Additionally, an image sensor is positioned to receive the filtered beam and produce an output signal associated with the filtered beam. Optionally, the apparatus can include circuitry for collecting and processing the image data to generate reconstructed images from the filtered images. Alternatively this circuitry can be located elsewhere and still form part of the system.

In one such apparatus embodiment, a removable or reconfigurable filter is arranged in the pupil plane to facilitate the modeling of the high NA effects of the lithography apparatus. The apparatus being configured to enable different filters to be interposed into the pupil plane from a library of filters until a sufficient number of images are captured enabling a reconstructed image to be formed from the raw data captured by the detector. In an alternative approach the filter can comprise reconfigurable filters having a programmable set of optical characteristics that enable different images to be obtained. The different images can be obtained such that they can be combined into a reconstructed image that models high NA optical effects.

In another alternative embodiment the magnification optics include beam splitting optics configured to generate at least two patterned beams which are directed into a corresponding plurality of apertures. Each aperture having a different filter and an associated detector. Thus, several filtered images can be captured simultaneously thereby enabling accelerated inspection.

In another method embodiment a method of comparing with reference or baseline patterns is disclosed. The method involves illuminating a portion of a mask reticle to produce a patterned beam and filtering the beam to construct a plurality of filtered beams that conform to a model of the optical performance of a photolithography apparatus to produce a plurality of filtered beams. The plurality of filtered beams are detected to produce image data which is processed to obtain a reconstructed image or the imaged portion of the mask. The reconstructed image can be processed with reference or baseline images to generate comparison data used to characterize the mask.

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which:

FIGS. 3(a)-3(i) are a collection of simplified schematic depictions illustrating some distinctions between defects and lithographically significant defects.

It is to be understood that, in the drawings, like reference numerals designate like structural elements. Also, it is understood that the depictions in the Figures are not necessarily to scale.

DESCRIPTION OF SPECIFIC EMBODIMENTS

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The following detailed description describes various embodiments of a method and approach for detecting defects in a mask reticle or comparing a mask reticle with an intended pattern.

Figure 1A:
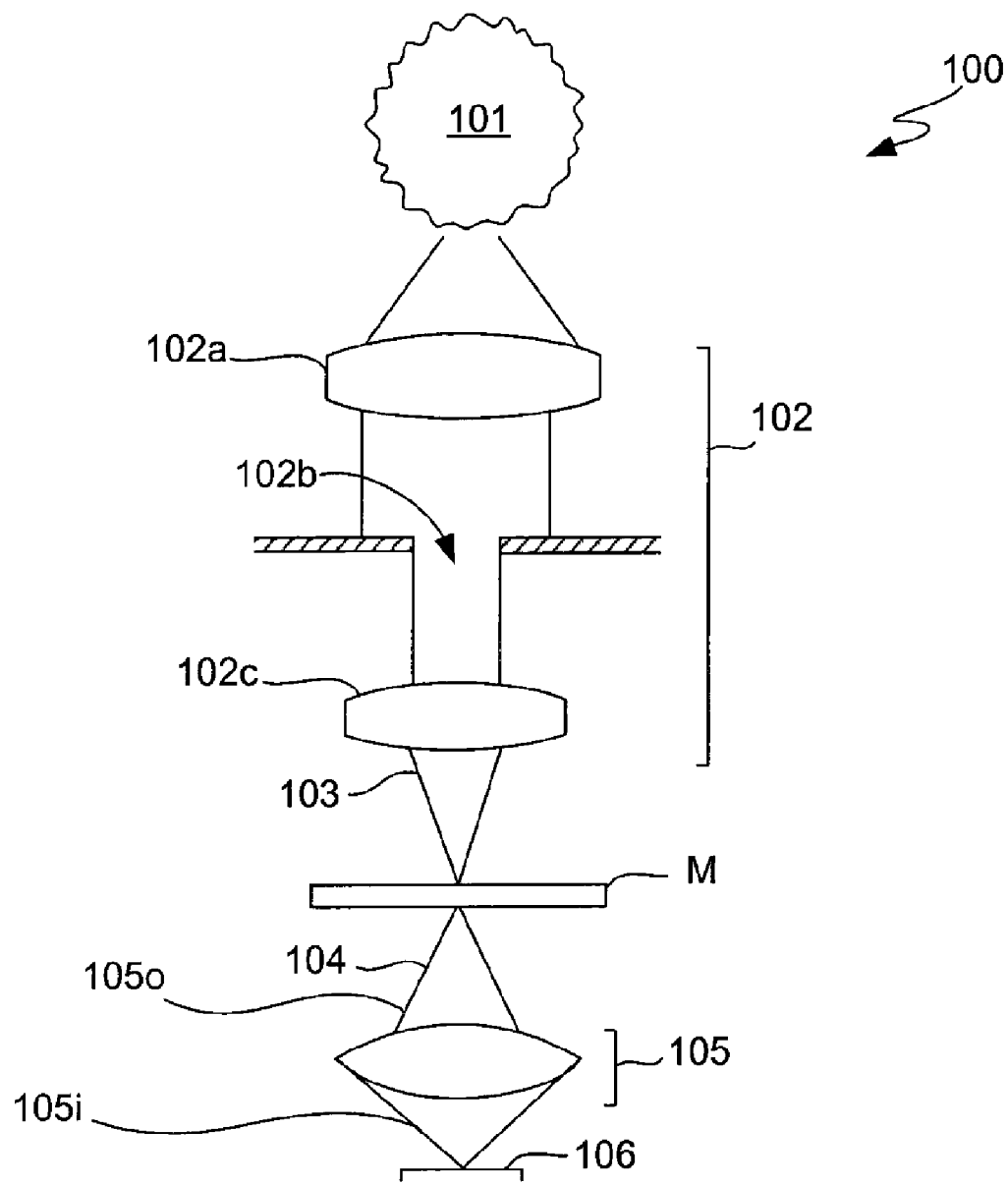
FIG. 1A is schematic depiction of a prior art photolithography apparatus, such a stepper, used to pattern a substrate.
Figure 1B:
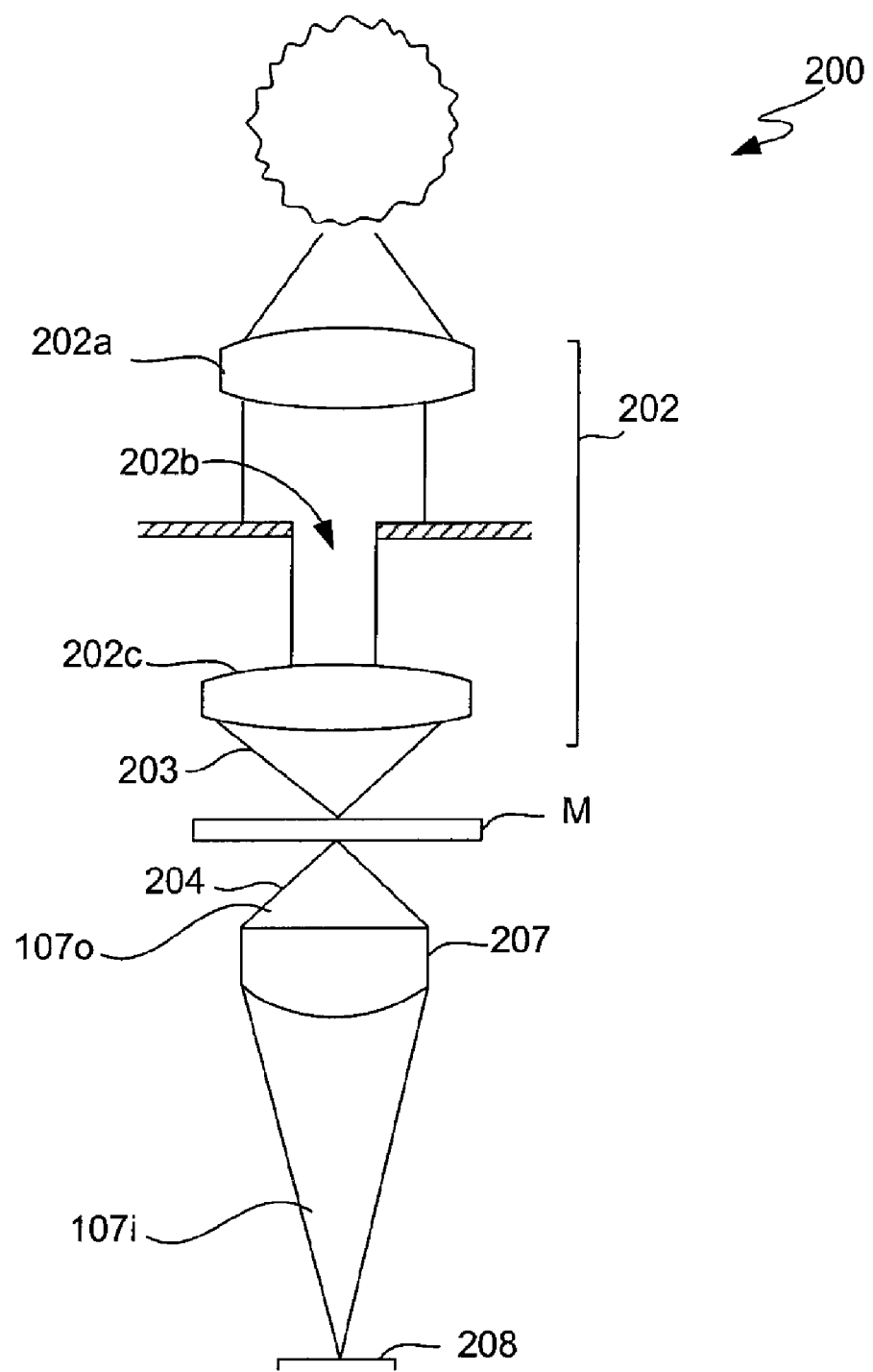
FIG. 1B is schematic depiction of a prior art inspection apparatus used to conduct mask inspection.
Figure 2:
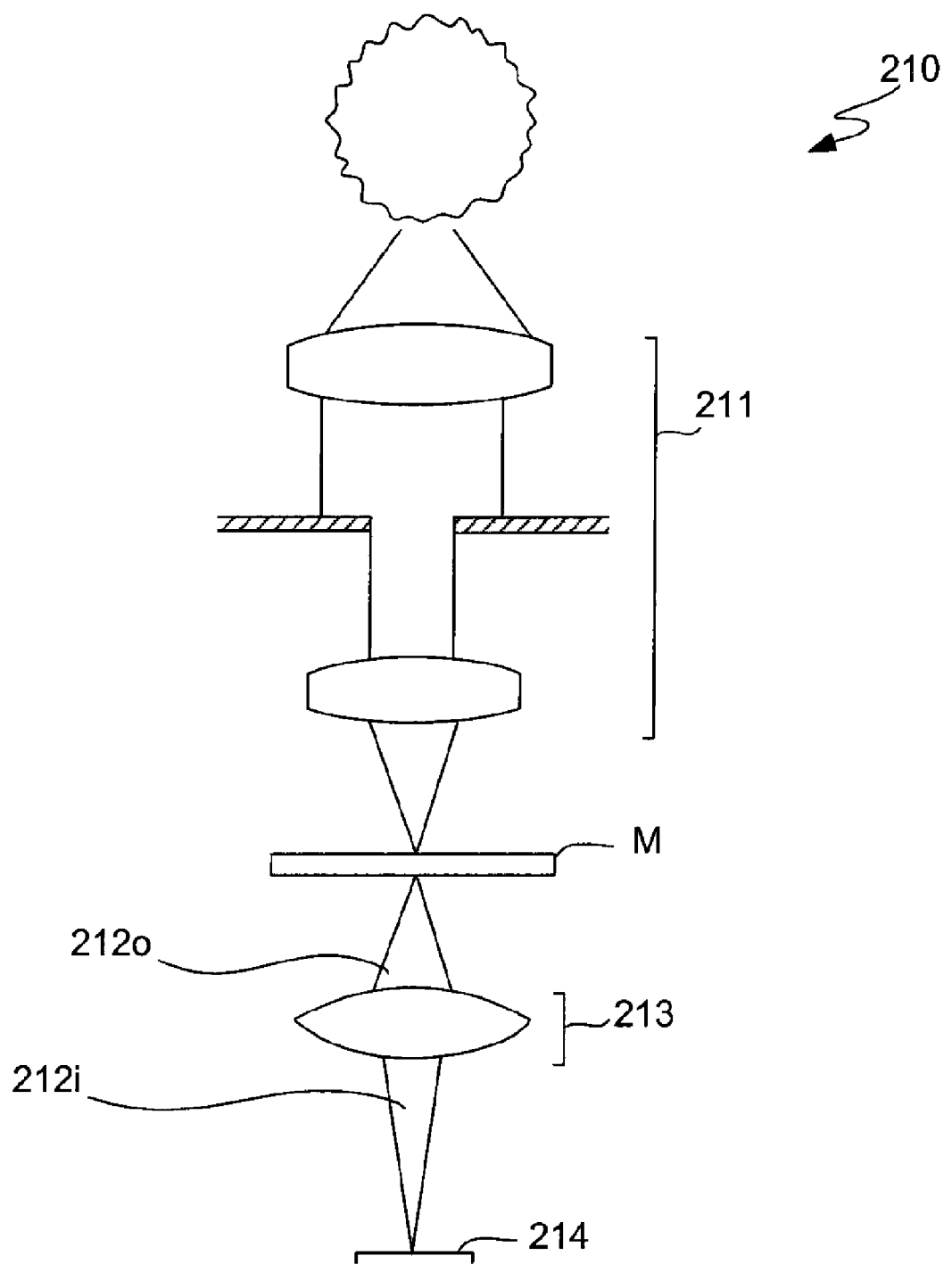
FIG. 2 is schematic depiction of another prior art inspection apparatus used to conduct mask inspection.

One of the problems in the present art is that inspection is done with a different lens system than the lens system used to form photolithographic patterns in the substrate. Commonly, a photolithographic patterning tool (e.g., scanners, stepper s, and the like) is constructed having a high image NA (above about 0.85). Thus, for example, steppers are generally low illumination, high NA, reduction systems (See, e.g., FIG. 1A). In contrast, inspection systems are high illumination, low NA, magnification systems having low image NA (NA less than about 0.30) suitable for examination and inspection of the same substrate, (See, e.g., FIG. 1B or 2). The reason for this discrepancy is quite simple. Inspection and defect detection is accomplished by projecting the mask pattern onto a CCD or other optical detector 208. Due to the (comparatively) large size of the photosensitive elements (e.g., in the range of about 10 μm) of the detector, considerable magnification is required to image mask features formed on a nanometer scale. Such nanometer scale resolution is required to properly image patterns and potential defects. Accordingly, low NA high magnification optics are required to achieve the necessary resolution. Although these optics are excellent for finding defects, they are not particularly useful for discerning the difference between lithographically significant defects and other defects in general. This is because of the differences in high-NA effects in image formation between a stepper and a reticle inspection tool. Thus, image produced by the two types of optical systems are not directly comparable.

However, the inventors have discovered that an ordinary inspection tool can be modified to capture the high NA effects of a photolithographic tool. The inventors have further discovered that by modifying the inspection tool in this manner that they can confine defect detection to only lithographically significant defects. This presents a significant step forward in the state of the art.

Moreover, the inventors have discovered that the same principles can be extended to AIMS review devices Additionally, the same inventive principles can be adapted to embodiments for pattern verification wherein the simulated reference patterns generated from an ideal mask design (either aerial images or resist-modeled images) or an intended wafer pattern can be compared to image pattern that are actually produced by the mask (these may also be aerial images or subject to resist modeling or even models of etching processes performed on a wafer).

As is generally is known to those having ordinary skill in the art, the Abbe formulation can be used to describe the intensity image formed in a layer of photoresist. Such an image can be projected into the photoresist layer of a substrate using, for example, a high NA stepper system. Accordingly, the Abbe formulation describes:

$$I(r) = \int S(k) \|E(r,k)\|^2 dk = \int S(k)(E_x^2(r,k) + E_y^2(r,k) + E_z^2(r,k)) dk \qquad \text{[Eqn. 1]}$$

where S(k) refers to the illumination intensity from a point source in direction k;

where E(k) represents a full 3-D vector at an X-Y plane location r at a desired depth in a photoresist and is a simplified notation for E(r, k);

Additionally, in a most generalized form, E(k) can be generalized as follows:

$$E(k) = \begin{bmatrix} E_x(k) \\ E_y(k) \\ E_z(k) \end{bmatrix} \qquad \text{[Eqn. 2]}$$

-continued $$= \begin{bmatrix} h_{xx}(k) & h_{xy}(k) & h_{xz}(k) \\ h_{yz}(k) & h_{yy}(k) & h_{yz}(k) \\ h_{zx}(k) & h_{zy}(k) & h_{zz}(k) \end{bmatrix} \otimes \begin{bmatrix} e_x(k) \\ e_y(k) \\ e_z(k) \end{bmatrix}$$

$$= \begin{bmatrix} h_{xx}(k) & h_{xy}(k) & h_{xz}(k) \\ h_{yz}(k) & h_{yy}(k) & h_{yz}(k) \\ h_{zx}(k) & h_{zy}(k) & h_{zz}(k) \end{bmatrix} \otimes$$

$$\left( \begin{bmatrix} A_{xx}(k) & A_{xy}(k) & A_{xy}(k) \\ A_{yx}(k) & A_{yy}(k) & A_{yz}(k) \\ A_{xz}(k) & A_{zy}(k) & A_{zz}(k) \end{bmatrix} \cdot \begin{bmatrix} P_x(k) \\ P_y(k) \\ P_z(k) \end{bmatrix} \right)$$

where A is the generalized form of the mask transmittance or diffraction function;

and where H describes the aggregate effects of the imaging pupils of a stepper, vector interference of electrical field within the resist, Fresnel refraction in wafers films stack (including such things as resist, TARC (top anti-reflective coating), BARC (bottom anti-reflective coating), immersion liquid and so on. Also, $\otimes$ stands for convolution in the spatial domain and $P_n(k)$ stands for polarization state an amplitude of the illumination source in direction k.

An equivalent representation describes the relation in the Fourier domain as follows:

$$\begin{bmatrix} M_{xx}(u,k) & M_{xy}(u,k) & M_{xz}(u,k) \\ M_{yx}(u,k) & M_{yy}(u,k) & M_{yz}(u,k) \\ M_{yz}(u,k) & M_{zy}(u,k) & M_{zz}(u,k) \end{bmatrix} \begin{bmatrix} F\{e_x(k)\} \\ F\{e_y(k)\} \\ F\{e_z(k)\} \end{bmatrix}$$  [Eqn. 2a]

where $M_{mn}(u,k)$ describes pupil functions of the projection optic system as a matrix of high NA correction filters. Typically, these filters can be described as phase and amplitude modulation filters that correct the signal to model for the high image NA effects of stepper (which has been replaced in the inspection tool by a low image NA optic enabling high magnification). In some embodiments the pupil functions are polarization specific pupil filters. In some embodiments these filters can take the form of a Jones matrix. $F\{e_n(k)\}$ describes an associated Fourier transform of the electrical field after the mask diffraction. Typically, the high NA correction matrix can describe the effects of the high NA projection optic system (such as a projection optic system of a stepper system used to print photolithographic patterns into a photoresist layer of a target substrate). Commonly, this matrix can capture polarization-dependent phase and amplitude modulation effects induced by the modeled optical system. In some implementations the high NA correction matrix is a Jones matrix. Also, the high NA correction matrix can function as a set of phase and amplitude correction filters that account for high numerical aperture (NA) effects induced by the projection lithographic optics. Thereby enabling a high magnification inspection system (with a relatively low image NA) to model optical effects produced by the lithographic tools used to print mask patterns to a substrate.

Although, the high NA correction matrix M includes components in all three dimensions, the inventors point out that it can be simplified because the matrix only has two degrees of freedom because the electric field is perpendicular to its direction of propagation (k). Thus the high NA vector effects can be described by a 2D mask transmittance function A and a simplified high NA correction matrix M as described below.

$$E(k) = \begin{bmatrix} E_x(k) \\ E_y(k) \\ E_z(k) \end{bmatrix} = \begin{bmatrix} M_{xx} & M_{xy} \\ M_{yz} & M_{yy} \\ M_{zx} & M_{zy} \end{bmatrix} \otimes \begin{bmatrix} A_x \\ A_y \end{bmatrix}$$  Eqn. 3 where M can aggregate at least the high NA imaging effects inside the photoresist layer, Fresnel refraction effects at the interfaces of the film stack (e.g., at TARC, BARC, photoresist, immersion fluid and other interface effects), TE/TM transmission/reflection and standing wave effects within the photoresist layer, and radiometric correction as well as other effects.

Eqn. 3 can be implemented in a number pupil filter embodiments in a reticle inspection tool. In one embodiment, mask de-polarization effects are treated as negligible. Accordingly, inspection tool illumination only need mimic the effects in the intensity domain and need not mimic the polarization state of the stepper illumination. In another implementation the mask de-polarization is not treated as negligible. In this implementation, inspection tool mimics the stepper illumination in both intensity and polarization domains.

Mask de-polarization refers to the phenomenon encountered when the polarization state after diffraction by a mask is sometimes slightly different from the polarization state of the illumination. If this effect is treated as negligible, then Eq. 3 can be implemented as a sum of images acquired with different imaging pupils. For example, if the stepper illumination is X-polarized, then we know that $A_y$ in Eq. 3 should always be zero, thus the intensity in Eq. 1 can be simplified as $I(r)=\int S(k)\|$
$\vec{E}(r,k)\|^2 dk = \int S(k)(\|E_x(r,k)\|^2 + \|E_y(r,k)\|^2 + \|E_z(r,k)\|^2) dk =$
$\int S(k)\|M_{xx} \otimes A_x\|^2 dk + \int S(k)\|M_{yx} \otimes A_x\|^2 dk + \int S(k)\|$
$M_{zx} \otimes A_x\|^2 dk$  [Eqn. 4]

i.e. sum of three images captured with three different pupil filters. Similarly, an un-polarized illumination on stepper can be simulated with sum of six images from the inspection tool (three for x-polarization and three for y-polarization).

Thus, using six filters, the inventors have the ability to create a reconstructed image of the photolithographic pattern as is present in the photoresist layer. For example, a set of six images can be collected and then processed together, for example by image summing, to create a reconstructed image that is nearly identical to that which the high NA system would have projected through the photolithographic system (e.g., stepper, scanner, etc) to obtain an aerial image. In fabrication such an aerial image is projected into a photoresist layer to expose a pattern for a substrate. In this process, the aerial image can be processed with a resist model (that models photoresist behavior upon exposure) to obtain a so-called resist-projected image.

It is to be noted that when the mask introduces polarization effects the process is modified slightly to incorporate the polarization effects induced by the mask. Methods of accounting for this will be discussed in detail below (for example with respect to paragraph [0096] et seq).

Additionally using this model, the inventors have discovered that further simplifications of the high NA correction matrix M can be made. The inventors have observed that:

$M_{yx}=M_{xy}$ $M_{yy}$ is equivalent to $M_{xx}$ if rotated 90 degrees
$M_{yz}$ is equivalent to $M_{xz}$ if rotated 90 degrees Thus, the high NA correction matrix M can be further simplified to a three element matrix.

Thus, in brief a set of filtered images collected with a low NA high magnification system can be collected and summed together to generate reconstructed image which very closely emulates the actual pattern produced by the high NA system. The importance of this will be explained briefly.

Thus, it has been explained that by selectively filtering a high magnification low NA image, a plurality of filtered images can be captured and summed together to generate a reconstructed image that models the actual image produced by a mask using a high image NA projection optical system. This can be used to selectively detect photolithographically significant defects during inspection. Embodiment methods and apparatuses and a specific implementation for accomplishing this will now be described.

Figure 4:
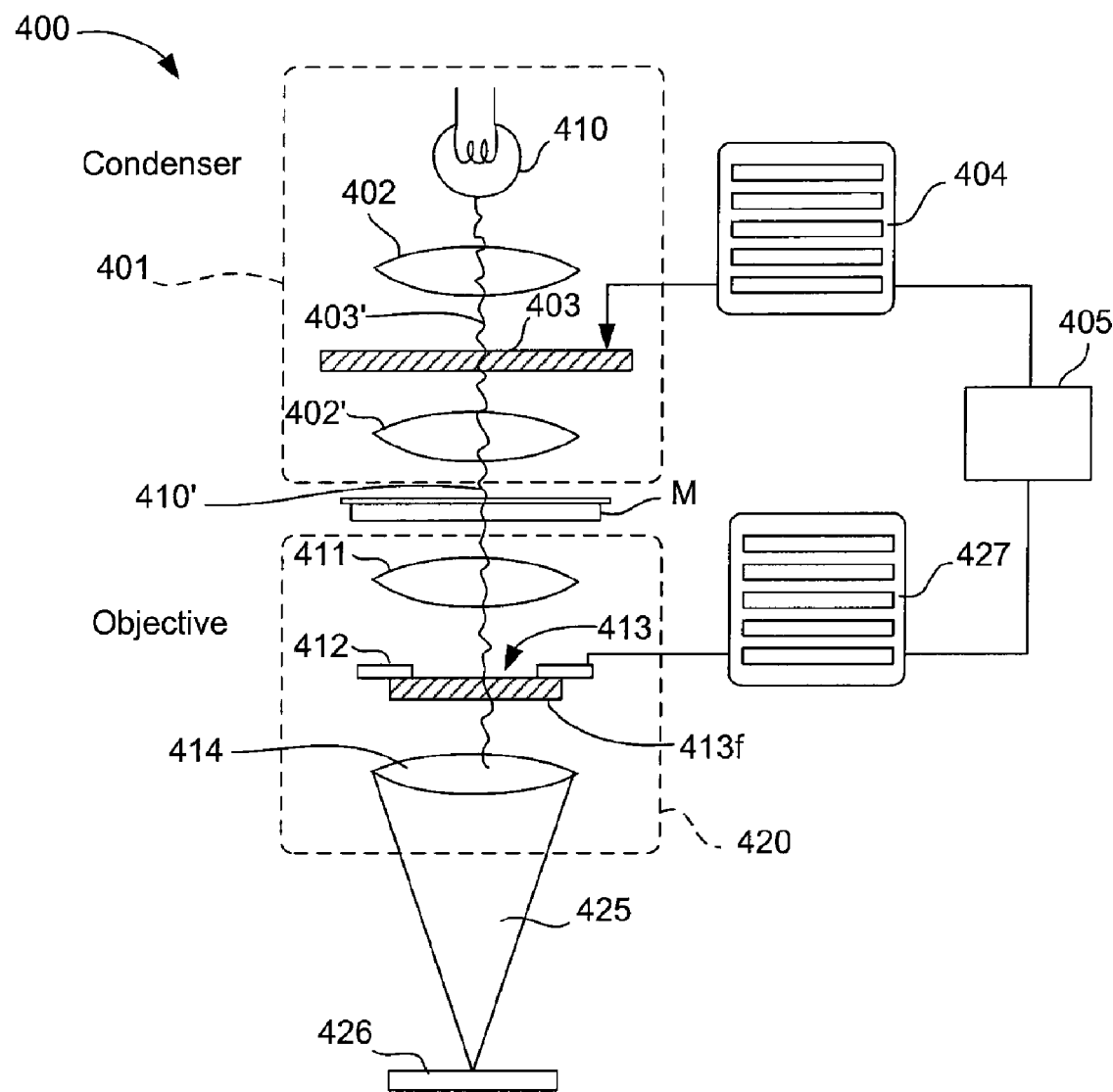
FIGS. 4 and 5 are simplified figurative illustrations depicting inspection apparatus embodiments constructed in accordance with the principles of the invention.

FIG. 4 illustrates one example embodiment of an inspection tool 400 constructed in accordance with the principles of the invention. The tool is configured to do defect detection and pattern verification for a mask reticle. The tool includes a first optical stage generally comprising an illumination optical system 401. In one suitable embodiment, the illumination optical system 401 matches the optical parameters of a lithography apparatus (e.g., a stepper for example) that will be used to conduct lithography with the mask reticle mentioned above.

The illumination optical system 401 includes an illumination source 410 directs a light beam 410' into illumination optics 402, 402' of the inspection tool 400. Such illumination sources can be any of the ordinary optical devices used by those having ordinary skill or any equivalents thereof. Such may include, but are not limited to, lasers or filtered high intensity lamps and so on. For example, a 193 nm laser can be employed.

The illumination optics are schematically represented here in extremely simplified form as elements 402, 402'. The illumination optics here can be configured to model the illumination intensity parameters of the lithography system. This can include light intensity and illumination aperture. The illumination optic system 401 can include, for example, collimating optics 402 and a focusing or collimating optic 402'. The inventors point out that the optics are not limited to such, merely that the discussed embodiment match the optical characteristics of the lithography apparatus discussed above. This includes an illumination pupil plane 403 having an aperture 403'. The aperture 403' can be one of many aperture configurations that form a library 404 of apertures with the desired aperture implemented at the time of inspection. The apertures can be of any shape or size as well as a plurality of apertures. Alternatively, the aperture 403' can comprise a spatial light modulator (SLM) arranged in the pupil plane. The SLM can be reconfigured as needed. The SLM can be configured from a library 404 of stored preset SLM settings that model a desired aperture or it can be set on an as needed basis in accord with known specifications. This can be implemented with control and/or storage circuitry 405 used to configure the system 400. Commonly, this circuitry comprises a suitably configured microprocessor. The microprocessor 405 can for part of the apparatus or comprise remotely located circuitry such as a networked computer or other control apparatus. In general, the idea here is that the controllable illumination filters 404 can be used mimic or reproduce the illumination intensity and exposure properties of a number of different steppers if desired. This prevents the need to provide completely new optical trains each time a new lithography tool is introduced into the system.

The illumination optical system 401 directs the filtered illumination beam 410' onto a selected portion of a mask reticle M. In one embodiment of the invention, the parameters of the illumination optical system 401 are designed to match intensity parameters of a high NA lithographic patterning tool. In another embodiment, the parameters of the illumination optical system 401 are designed to match the intensity and the polarization of the high NA lithographic patterning tool.

Once the mask M is illuminated by the beam 410' a pattern is generated forming a patterned illumination beam that is directed into a second optical stage 420 generally referred to here as projection optics or magnification optics. The magnification optics here form a filtered beam 425 that is directed onto a detector element 208 where it produces a signal corresponding to the received light.

In the depicted embodiment, the second optical stage 420 includes a condenser or collimating optic 411 that generally collimates the patterned beam and directs it to another aperture 413 positioned in a pupil plane 412 of the second optical stage 420. A filter 413$f$ is positioned in the aperture to generate a filtered beam 425 which passes through the remaining portion (e.g., magnification optic 414) of the second optical stage 420 and is directed onto a detector element 426 where raw image data is generated.

The aperture 413 and filter 413$f$ are configured to model vector elements of the high NA correction matrix for the high NA lens systems described above. As described above, the filters can be configured to model the image in as projected into the resist or to define an aerial image for the mask. The filter 413$f$ can be a filter selected from among a library 427 of pre-generated filters that can be slid into position as needed. Or alternatively, in some embodiments the filter may be modeled by an SLM. The filter element 413$f$ can be controlled using the same circuitry as used to control the aperture 403' (as shown here) or alternatively other electronic circuitry can be used if desired.

The detector 426 receives image information in the form of raw image data. A single filtered image is, in and of its self, not useful in detecting defects in the manner suggested in this patent. Further raw images are required. Each raw image is taken of the same spot using a different filter 413$f$. For example, the six filters of the high NA correction matrix (e.g., a Jones Matrix) as referred to in Eqn. 3 can be used to obtain the six raw images. These raw images can be processed together to obtain a reconstructed image. In the reconstructed image the high NA effects are replicated and the image created by the mask can be obtained. This has not been possible with the prior art approaches. These reconstructed images can be compared with the various reference images to obtain pattern verification and/or defect detection processes. For example, the reconstructed image can be processed with a resist model to obtain a "resist-modeled image" which is intended to model the effects of the pattern on a photoresist layer used on an actual wafer. The idea being that the resist model will mimic the precise effects of the lithographic imaging (here the reconstructed image) a process wafer to reveal the pattern as printed. This can be compared with the original design file (i.e., the circuitry pattern the process engineer desires to print onto the wafer (i.e., the "pre-OPC" pattern)) to "verify" that the mask will print the pattern onto wafer as desired. In another example, the reconstructed image can be processed with a resist model and a model of etching performance (based on the actual etching process to be used) to obtain a "resist and etch modeled image" which is intended to model the effects of the pattern on a photoresist layer and then subsequently etched to effect pattern transfer onto an actual wafer. The idea being that the resist and etch modeling will mimic the precise effects of the lithographic imaging and etching of a process wafer to reveal the pattern as actually formed on the wafer. This can be compared with the original design file (i.e., the circuitry pattern the process engineer desires to print onto the wafer (i.e., the "pre-OPC" pattern)) to "verify" that the mask will enable the correct pattern to be formed on the wafer as desired.

Additionally, various reference images can be used to verify the mask pattern and to conduct defect inspection of lithographically significant defects in accordance with the principles of the invention. Examples of these approach will be explained further below.

The inventors point out that the methodologies disclosed herein can be used to determine if the mask is correct (pattern verification) and/or whether the pattern to be printed in the resist is correct (defect detection). Importantly, this invention includes embodiments capable of performing this such that only the lithographically significant defects are identified. This presents a substantial increase in efficiency over the prior art methods. Additionally, as discussed in elsewhere in this patent, the process can be accelerated to obtain this information using even fewer images. For example, as few as three images can be used to obtain an accurate and useful reconstructed image in accordance with the principles of the invention.

Figure 5:
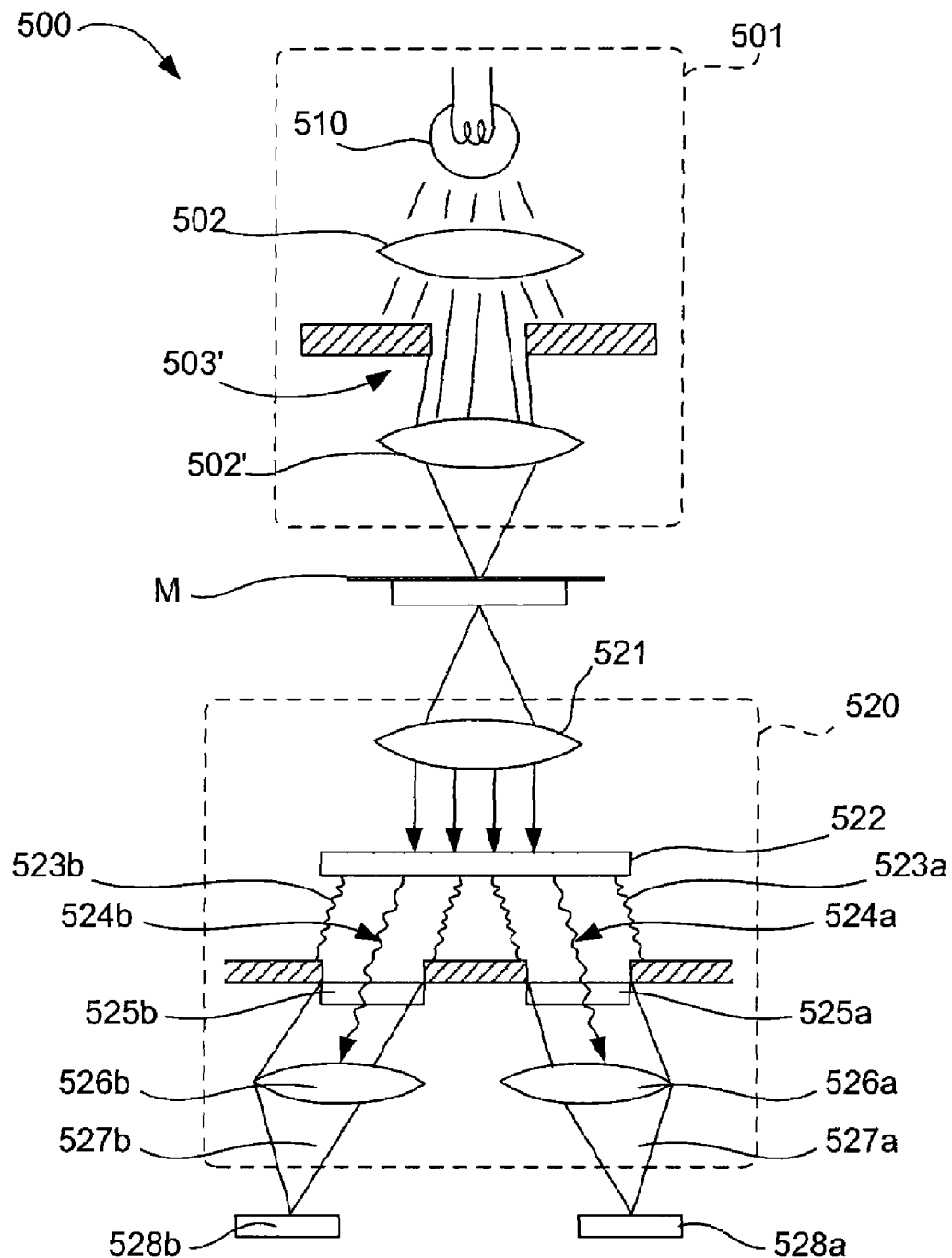

FIG. 5 depicts yet another embodiment capable of capturing more than one filtered image at a time to even more quickly capture raw image data and thereby accelerate the inspection process. The example embodiment depicted in FIG. 5 is another of an inspection tool 500 constructed in accordance with the principles of the invention. The tool is configured to do defect detection and pattern verification for a mask reticle. The tool includes a first optical stage 501 that is configured nearly the same way as the stage 401 of FIG. 4. As such the illumination optical system 501 can be configured to match the optical parameters of a lithography apparatus (e.g., a stepper for example) that will be used to conduct lithography with the mask reticle mentioned above.

As does 401 of FIG. 4, the present illumination optical system 501 includes an illumination source 510 that directs a light beam into illumination optic 502 through aperture 503' and into optic 502' where it is used to illuminate a mask reticle M. Also, as before, the illumination optics are schematically represented here in extremely simplified form as elements 502, 502' and can include, but are not limited to collimating optics, focusing optics, or other optical elements known and used by thos of ordinary skill or equivalents thereof. Again, the inventors point out that the optics of the discussed embodiment can match the optical characteristics of the lithography apparatus discussed above (although this is not required it has numerous advantages, not the least of which being the simplification of the filters associated with the high NA correction matrix).

As with the previous embodiment, the aperture is arranged in a pupil plane and can be selected from a library of many aperture configurations. Also, the aperture 503' can comprise an SLM arranged in the pupil plane. The SLM can be configured to modulate both amplitude and phase of the received light. Additionally, as before, the SLM can be reconfigured as needed. The SLM can be configured from a library of stored preset SLM settings that model a desired aperture or it can be set on an as needed basis in accord with known specifications. This can be implemented with control circuitry (such as shown in FIG. 4). As above, in one embodiment of the invention, the parameters of the illumination optical system 501 are designed to match those of a high NA lithographic patterning tool.

Once the mask M is illuminated, the beam produced is directed onto a second optical stage 520 generally referred to here as projection optics or magnification optics. The second stage optics 520 are configured to generate a plurality of patterned optical beams and individually filter the beams with different filter elements and capture the images which are later processed and combined to generate a reconstructed image as described briefly above and in detail below. This configuration is advantageous because it enables more than one filtered beam to be captured at the same time. Thus, inspection times can be further reduced.

A more detailed description of the second optical stage 520 is now provided. In the depicted embodiment, the second optical stage 520 includes a first optical element 521 (which can be any optical element but is typically a condenser or collimating optic). The optic 521 directs the beam into a multiple beam generating optic 522 that generate at least two output beams (Here, 523a, 523b). The beam splitting optic 522 can be of a number of types known to those having ordinary skill in the art. In one embodiment, the beam splitting optic 522 is a diffractive optic. Accordingly, two similar beams are produced and directed into an associated aperture, each having a different filter formed therein.

The apertures 524a, 524b and associated filter elements 525a, 525b are arranged in a pupil plane of the second optic system 520. The apertures 524a, 524b and associated filter elements 525a, 525b are configured to model one of the vector elements of the high NA correction matrix for the high NA lithography lens systems, such as described above. As described above, the filters can be configured to model the image in as projected into the resist or to define an aerial image for the mask. The filters 525a, 525b can be a filter selected from among a stored library of pre-generated filters that can be slid into position as needed. Or alternatively, in some embodiments the filters may be modeled by an SLM. The filter elements can be controlled using the same circuitry as used to operate other aspects of the device 500.

The filters 525a, 525b each have different optical parameters from each other. Additionally, in typical embodiments the filters can be phase shifting attenuating filters. Particularly suitable are phase shifting attenuating filters that model the functions of a high NA correction matrix (e.g., a Jones matrix) associated with a high NA photolithographic projection optical system. Typically, each filter optically modulates the beams in association with one of the elements of a correction matrix vector.

Each of the aperture/filters are associated with a second optical element 526a, 526b that focuses and projects the associated filtered beams 527a, 527b down onto an associated detector elements 528a, 528b where raw image data is generated. The second optical elements 526a, 526b can be configured as magnification optics to form separate filtered beams 527a, 527b that are directed onto separate detector elements 528a, 528b where it produces a signal corresponding to the received light. For example, raw image data from detector 528a is processed together with raw image data from detector 528b and with other associated raw image data taken of the same spot using a different filter. For example, the six filters of the high NA correction matrix as referred to in Eqn. 3 are used to obtain the six raw images, using a two-filter device only three image groups need be obtained. In other embodiments having more filters and detectors, even less time is required. These raw images are processed together to obtain a reconstructed image. As before, the reconstructed image replicates the high NA effects and the image picture printed by the mask (either aerial of in resist) is obtained. Critically, this enables inspection to be performed concentrating only on the lithographically significant defects.

The inventors now describe a method embodiment for practicing the invention. In general the embodiment defines a method for inspecting a surface to identify lithographically significant defects or alternatively to verify the correctness of mask patterns formed on a mask reticle.

Figure 6:
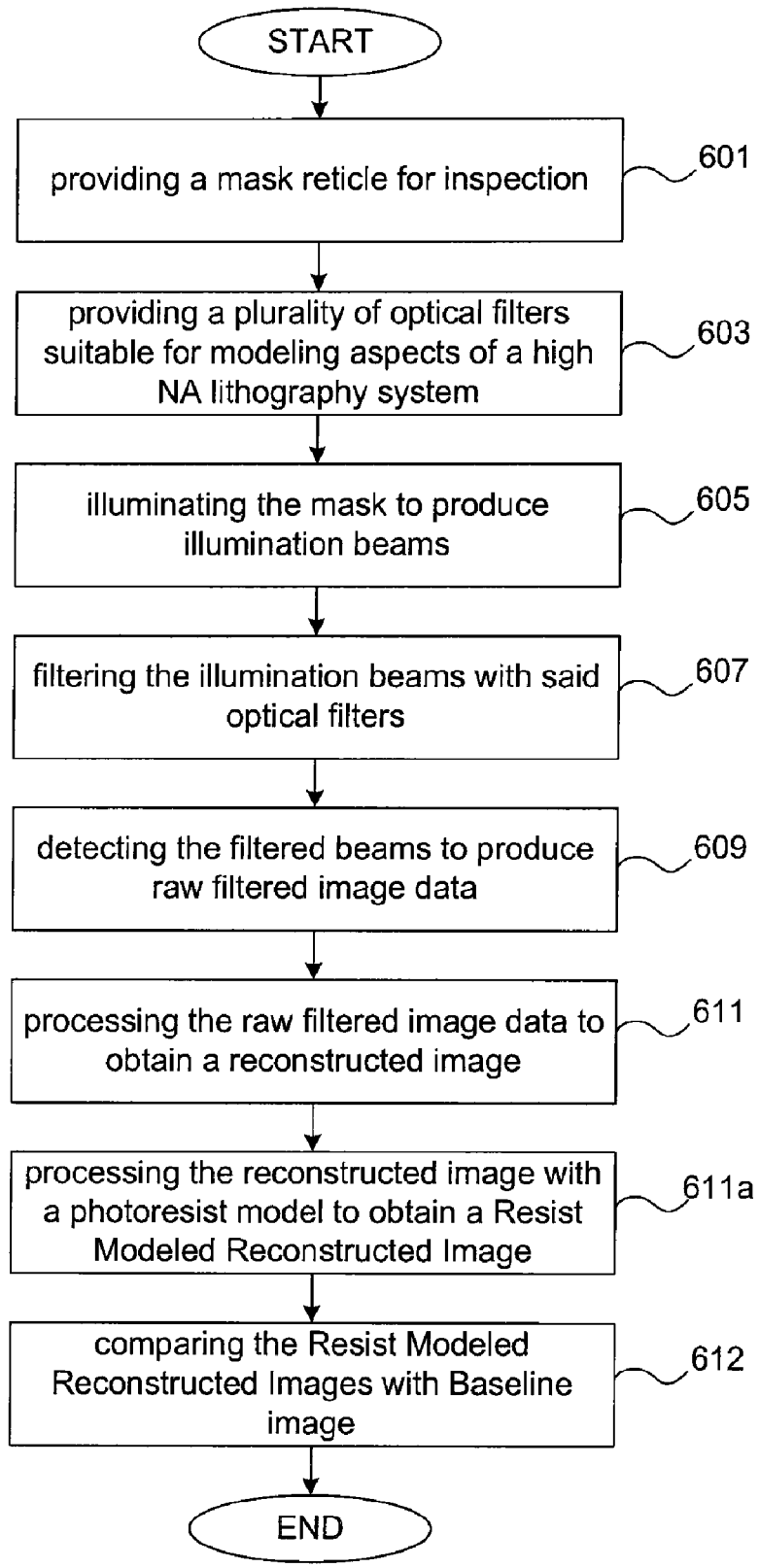
FIG. 6 is a simplified flow diagram illustrating a method embodiments and the operations used perform the embodiment in accordance with the principles of the invention.

FIG. 6 is flow diagram describing various operations used to in method embodiments of the invention.

The method involves providing a mask reticle (Step 601). The mask reticle being configured to achieve photolithographic transfer of a mask pattern onto a substrate using a lithography system having a high image NA.

The optical parameters of the high NA lithography system are processed to obtain filter values that characterize the optical system associated with the lithography system having a high image NA (Step 603). Typically, the optical parameters are those pertaining the projection optical system of a stepper system and associated film stack on the wafer. As indicated above, the filters can be defined to model a plurality of matrix values associated with a high NA correction matrix (e.g., a correctly configured Jones matrix) that characterizes the image NA of the lithography system. As described above, the parameters are an aggregate of the high NA imaging effects created by the stepper optics and film stack on wafer.

Where the profile desired is the resist projected image the filters are modeled to take into consideration a number of additional factors including, but not limited to, Fresnel refraction effects at the interfaces of the film stack (e.g., at TARC, BARC, photoresist, immersion fluid and other interfaces), TE/TM transmission/reflection and standing wave effects within the photoresist layer, and radiometric corrections. These filters can be modeled using mathematical models and known modeling programs to obtain the correct values which can include a plurality of matrix values associated with a Jones matrix that characterizes the high NA lithography system.

The embodiment further includes illuminating a portion of the mask reticle to produce a patterned illumination beam (Step 605). This involves projecting an optical beam through the mask that recreates the optical conditions during photolithographic pattern transfer (e.g., using the same source as that in the stepper optic). In some embodiments many essentially equivalent beams can be generated simultaneously.

The method further involves filtering the illumination beam with a filter element that models optical behavior of the high NA illumination system (Step 607). For example, a predetermined phase shifting and attenuating filter is interposed into the beam to create a filtered optical beam. Typically, the filters are configured to correct the optical properties of the signal to model the matrix values associated with the high NA lithography system (e.g., using an appropriate Jones matrix). Importantly, several different filters are used to create several filtered beams for each inspection site on the mask. Depending on the embodiment, the filtered beams can be generated one at a time or in groups of filtered beams. The idea being that several filtered beams are detected and processed together to form a reconstructed image that models the actual image produced by the mask when illuminated with a high NA lithography system. In other words, the filtered beams conform to a model of optical performance of the high image NA lithography system. The filters can be configured to generate a reconstructed aerial image or a reconstructed resist projected image. Each have different and valuable uses. In short, in one embodiment of the invention a plurality of filters are used for obtaining a plurality of filtered beams wherein the filters are configured to have optical performance associated with the matrix values of a high NA correction matrix adapted to recreate the optical effects of a high image NA system, so that summed filtered beam images conform to a model of optical performance of the high image NA lithography system.

A next operation involves detecting the plurality of filtered beams and producing raw image data associated with each filtered beam (Step 609). This process involved detecting the filter beams with photodetectors. Depending on the embodiment, this can be done sequentially (detecting one image after another) or simultaneously (detecting groups of images at the same time with several detectors). The raw data can be stored for subsequent processing.

Once all of the images have been captured they are processed (Step 611) to generate a reconstructed image that models the high NA effects of the photolithography tool (stepper) used to pattern wafers. As previously explained, this typically involves summing the image data taken for each site. For example, six images taken for a single site can be summed to construct an associated reconstructed image. All of the reconstructed image sites can be stored together to present a reconstructed image of portions of the mask. This reconstructed image is useful for a number of implementations. In one embodiment, the reconstructed image can be compared with the post-OPC mask design to verify mask fabrication accuracy. The reconstructed image can be compared with modeled reference images to obtain pattern verification and defect inspection information. For example, the mask design file (this can be the post-OPC mask file) can be rendered from a database of post-OPC design of the mask. This data is essentially a model of the intended post-OPC design of the mask. This data base file can then be processed through a lithographic simulation model (many such are known to those having ordinary skill in the art) to obtain a reference image that models an aerial image produced by the ideal (data base) post OPC mask. This can be compared with reconstructed aerial image obtained as briefly described above.

In another embodiment, this reconstructed image can undergo further processing to model a printed surface of substrate (Step 611a). Such processing includes processing the reconstructed images with a photoresist model that accurately reflects the photoresist behavior for a photoresist layer that is actually implemented on the surface of the substrate. This is a Resist Modeled Reconstructed Image. Thus, after modeling all the lithographically insignificant defects are omitted from the inspection. Additionally, none of the resolution enhancement structures or other non-printed features are present in the Resist-Modeled images. Thus, the Resist-Modeled Reconstructed Image is also useful for a number of implementations.

Finally, in another optional operation, the Resist Modeled Reconstructed Image can be compared with further reference (baseline) images to conduct defect detection or pattern verification (Step 613).

For example, in one implementation, a reference image can be obtained as follows. The post-OPC mask design database can be processed through a lithographic simulation of the relevant lithographic tool (as described above) to produce a simulated aerial image that models the predicted lithographic behavior of a database mask projected through the lithographic tool in question. Such reference or baseline image is useful for comparison with a reconstructed image of the type described above. Comparison of the reconstructed image with the simulated aerial image is one method of enabling defect detection.

Another reference can be generated by further processing the simulated aerial image (taken from the database model) together with a model of photoresist behavior to obtain a simulated resist modeled image. This can be compared with a resist-modeled reconstructed image to conduct reticle inspection that advantageously detects only those defects having lithographic significance. This involves comparing the pattern as it will be printed by the mask under inspection (the Resist Modeled Reconstructed Image of 611a above) with a database simulation of mask, lithographic tool, and photoresist. Additionally, various lithographic parameters can be varied (e.g., focus, exposure dose, etc.) to model the mask through a range of parameters to inspect for defects throughout the range of parameters that define the process window.

Additionally, pattern verification can also be performed using at least the following disclosed approaches. As described above, the reconstructed image can be processed through various models to obtain a resist-modeled image of the mask reticle pattern (or the image can be further processed with an etch performance to obtain an etch-modeled image). This is the pattern that will be formed on the wafer after processing using the mask and associated photolithographic processes. This pattern is comparable to the intended design pattern. This intended design is the wafer pattern (i.e., the pre-OPC pattern intended to be formed on the wafer). This can be compared with the resist-modeled reconstructed image (or the etch the etch modeled reconstructed image) to conduct pattern verification. This system can be modified using design rules and other factors that take into consideration standard errors in the fabrication processing. Additionally, various lithographic parameters can be varied (e.g., focus, exposure dose, etc.) to model the mask through a range of parameters to verify (or inspect for defects) through out the range of parameters that define the process window. Typically, the optical design rules and other limiting parameters are employed as a threshold to model whether the mask is a satisfactory match for the pattern in the intended pre-OPC design pattern. In this way the mask can be verified to determine whether it is satisfactory for its intended purpose (defects or not). One truly advantageous feature of the disclosed method is that instead of the many numerous checks made to obtain verification in the past, one embodiment of the invent only needs compare the pre-OPC database (the intended pattern) with the reconstructed and resist-modeled image produced by the actual mask. This is a substantial shift in efficiency and speed.

The following illustration and description (including added Appendix) illustrate one simplified example implementation for generating a suitable set of filters that can satisfactorily model a high NA stepper system in accordance with the principles of the invention. For example, referring to the Eqns. 3 & 4, several simplifications can be made. Thus only three filters need be used. Additionally, by treating the BARC (Bottom Anti-Reflective Coating) as perfect, no standing wave pattern is formed in the resist layer.

And also, if the following further simplifications are made, i.e., that there is no TARC and that the absorption of the immersion fluid is negligible, the following results can be obtained. In one example, three filters are obtained by using a Matlab© script. If we input the following parameters:

NA=1.2;
n of the immersion liquid is 1.4366;
the (n, k) values for the resist are (1.7, 0.056) respectively;
the resist thickness is 120 nm and that the image is formed at the bottom of the resist; and
the exposure wavelength is 193 nm Then the three unique filters are described as follows.

Figure 7A:
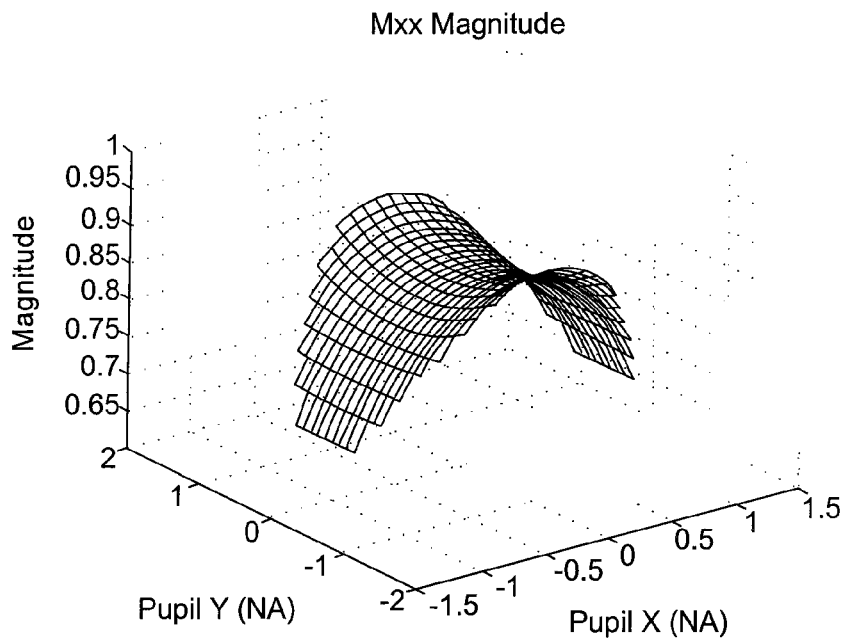
FIGS. 7(a)-7(f) are graphic depictions of phase and magnitude filtering parameters used in filter embodiments employed in some apparatus for inspecting masks to identify lithographically significant defects in accordance with the principles of the invention.
Figure 7B:
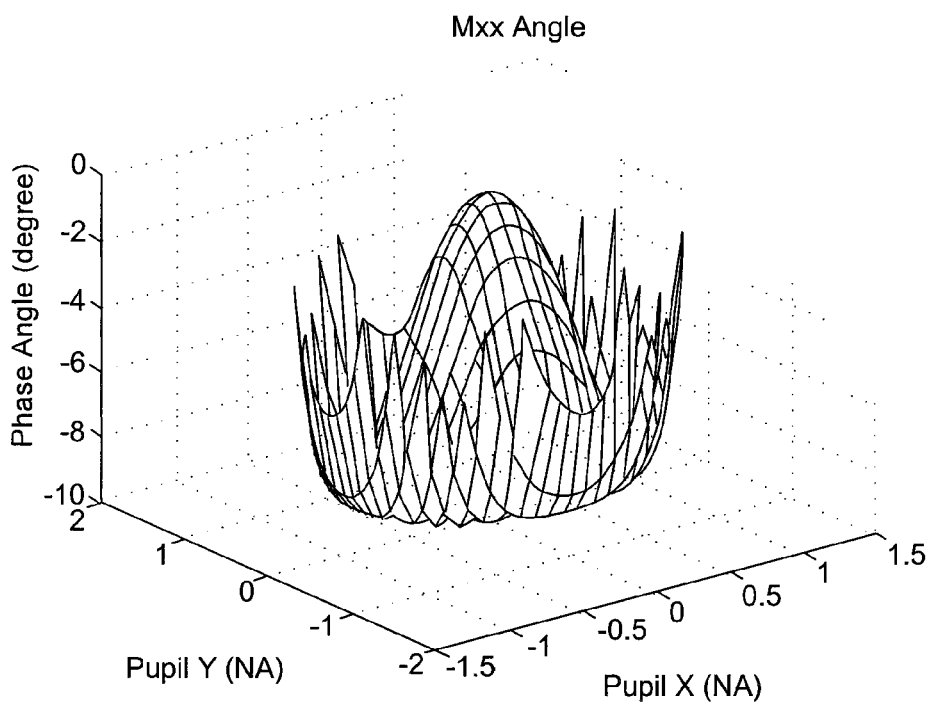

FIGS. 7(a) & 7(b) are graphical depictions of the optical properties of the first filter to be used in accordance with the principles of the invention. These characteristics describe a filter to be used for the $M_{xx}$ matrix element in the high NA correction matrix (which can be a Jones matrix). FIG. 7(a) describes the attenuation features of the filter. FIG. 7(b) describes the phase shift effects of the filter.

Figure 7C:
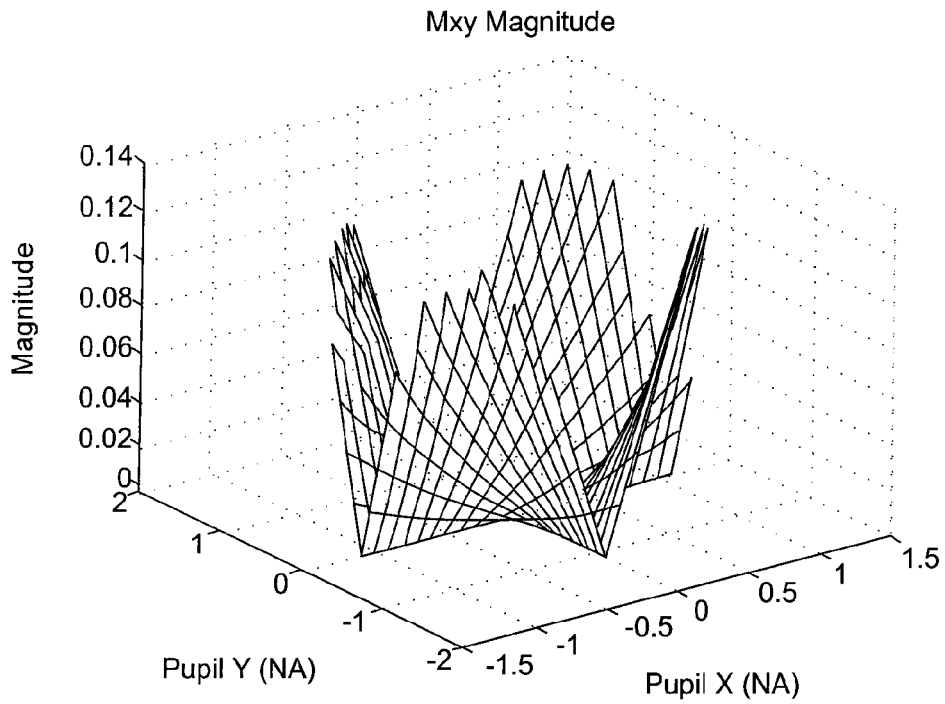
Figure 7D:
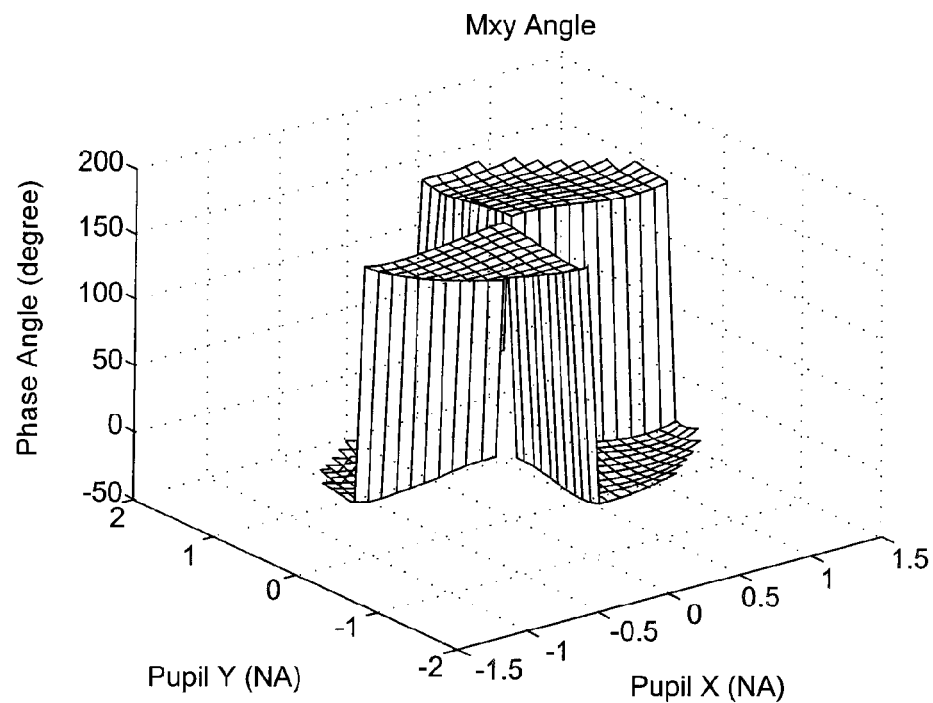

FIGS. 7(c) & 7(d) are graphical depictions of the optical properties of a second filter to be used in accordance with the principles of the invention. These characteristics describe a filter to be used for the $M_{xy}$ matrix element in the high NA correction matrix (which also can be a Jones matrix). FIG. 7(c) describes the attenuation features of the filter. FIG. 7(d) describes the phase shift effects of the filter.

Figure 7E:
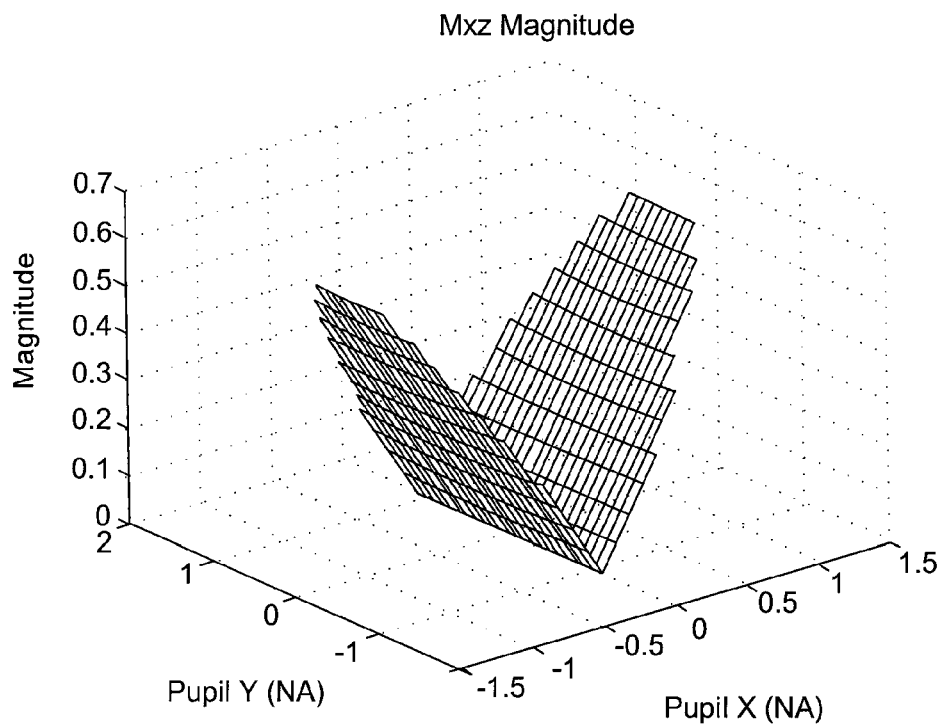
Figure 7F:
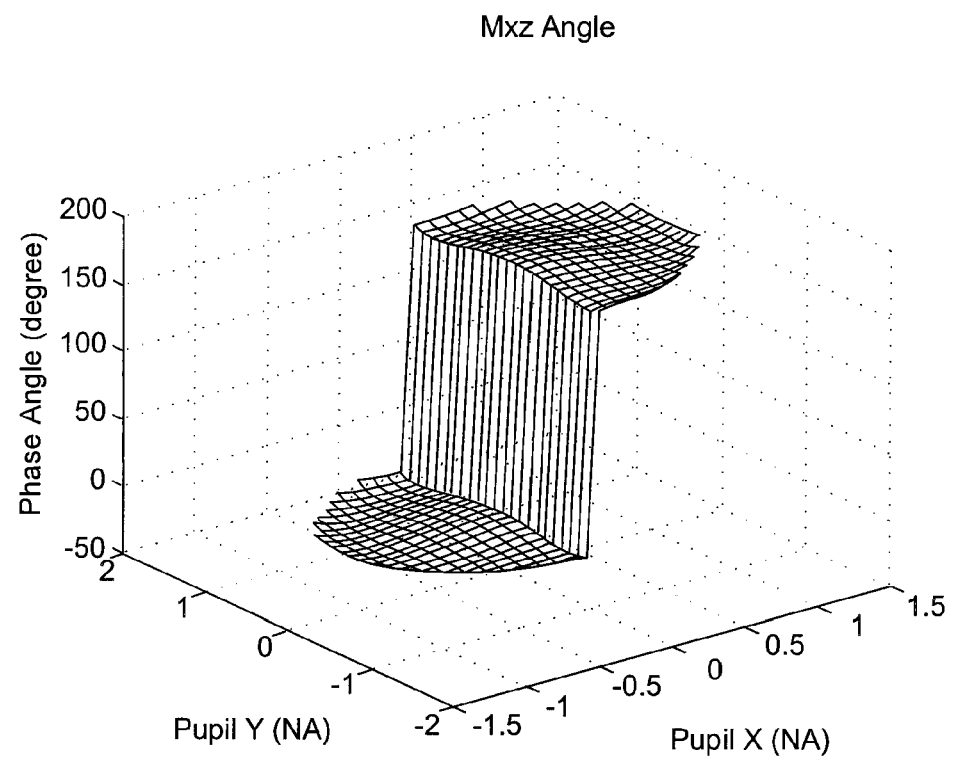
Figure 8:
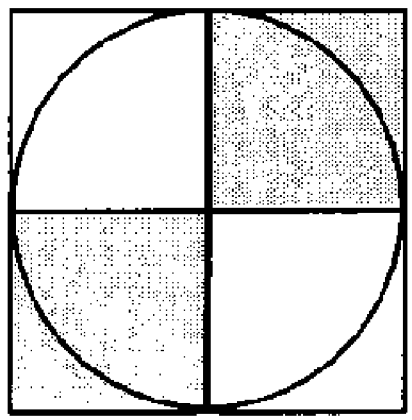
FIG. 8 is another graphic depiction of a set of phase filters that can be used with embodiments of the present invention.
Figure 8:
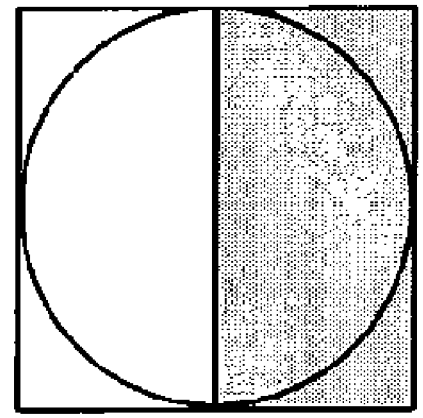

FIGS. 7(e) & 7(f) are graphical depictions of the optical properties of a third filter to be used in accordance with the principles of the invention. These characteristics describe a filter to be used for the $M_{xz}$ matrix element in the high NA correction matrix (which can also be a Jones matrix). FIG. 7(e) describes the attenuation features of the filter. FIG. 7(f) describes the phase shift effects of the filter The inventors make the following observations. The phase in the $M_{xx}$ term (and accordingly the $M_{yy}$ term) are so small as to be negligible and can then be ignored in most cases. The phase for both the $M_{xy}$ and $M_{xz}$ term can be addressed by very simple functions. For example, a pupil with two phase angles (0, π) can be implemented. For example, FIG. 8 describes implementations for both $M_{xy}$ and $M_{xz}$. In the FIG. 8 the darkened portions represent a phase of π and the white portions represent a phase of 0. Additionally, the attenuation filter parameters for $M_{xy}$ have a magnitude of only 10% of those for $M_{xx}$ and accordingly can be ignored for a NA of 1.2. The inventors point out that specific implementation details are examples only and the invention is not limited to such disclosed illustrating examples.

The inventors point out that under some circumstances where the illumination is polarized, the effects of mask depolarization are not negligible and should be taken into account during inspection. However, one difficulty in correcting for this effect is that the models describing such effects use amplitude values whereas the measuring systems used can only measure light intensity values. Previous approaches have suggested imaging with two coherent interfering beams to obtain such corrections. However, this has proven impractical as the associated interferometers are sensitive to the nanometer-level positioning errors common in such approaches.

However, the inventors have discovered that by modifying the processes disclosed above, and taking a few more images, the effects of mask depolarization can be accurately compensated for without resorting to interferometry.

The inventors again refer to Eqn. 3 which can be generalized as:

$$E(k) = \begin{bmatrix} E_x^{image} \\ E_y^{image} \\ E_z^{image} \end{bmatrix} = \begin{bmatrix} M_{xz} & M_{xy} \\ M_{yx} & M_{yy} \\ M_{zx} & M_{zy} \end{bmatrix} \otimes \begin{bmatrix} A_x \\ A_y \end{bmatrix} \quad \text{Eqn. 5}$$

As explained above, the inventors point out that the challenge has been to obtain amplitude information concerning phase effects without the need to use interferometry. For example, a direct calculation of each of the E terms, for example, $E_z^{image} = M_{zx}A_x + M_{zy}A_y$, is not generally possible.

However, the inventors have discovered that by taking additional images while correcting for polarization specific phase change effects accurate information can be obtained. The inventors contemplate that in accordance with the teachings provided herein, many methods of correcting for the polarization specific phase change effects can be employed.

In one example, a set of selectively chosen combinations of wave plates or polarization analyzer and the correction filters can be used to compensate for the polarization effects. In some example embodiments 18 (e.g., 6 for each component of E-field) variously filtered images can be taken to compensate for mask de-polarization effects to obtain a reconstructed image that accounts for high NA effects and mask induced polarization effects and the effect of the high NA system on the polarization effects.

$E_z^{image}$ can also be modeled similarly to Eqn. 4 as a series of intensity component images that can be summed together to obtain reconstructed images that compensate for high NA effects including polarization effects. For example:

$$E_z^{image}(\vec{x}) = \iint d^2 \vec{K}_s S(\vec{K}_s) |\iint d\vec{k} [m_{zx}(\vec{k})E_x(\vec{k}, \vec{K}_s) + m_{zy}(\vec{k})E_y(\vec{k}, \vec{K}_s)] \exp[i\vec{k} \cdot \vec{x}]|^2 \quad \text{Eqn. 6}$$

where $\vec{K}_s$ represents the illumination pupil position and where $\vec{k}$ represents the imaging pupil position. A first intensity component image $I_0$ can be obtained as follows. A polarizer can be introduced into an image optical path, for example, at the aperture 413. In the depicted approach the polarizer is oriented at a 45 degree angle, and the image is filtered using a pair of filters (of the type described above) implemented together as $\sqrt{2}(M_{31}+M_{32})$ to filter the polarized image which generates an $I_0$ such that:

$$I_0(\vec{x}) = \iint d^2 \vec{K}_s S(\vec{K}_s) |\iint d\vec{k} [m_{zx}(\vec{k})+m_{zy}(\vec{k})][E_x(\vec{k}, \vec{K}_s)+E_y(\vec{k}, \vec{K}_s)] \exp[i\vec{k} \cdot \vec{x}]|^2 \quad \text{Eqn. 7}$$

A second intensity component image $I_1$ is obtained. For example, referring to FIG. 4, a ½ waveplate can be introduced into the image optical path to induce a π phase shift between the x and y components of the electric field with a $\sqrt{2}(M_{31}-M_{32})$ pupil filter applied as above. This can be used to generate the second intensity component image $I_1$ such that:

$$I_1(\vec{x}) = \iint d^2 \vec{K}_s S(\vec{K}_s) |\iint d\vec{k} [m_{zx}(\vec{k})-m_{zy}(\vec{k})][E_x(\vec{k}, \vec{K}_s)-E_y(\vec{k}, \vec{K}_s)] \exp[i\vec{k} \cdot \vec{x}]|^2 \quad \text{Eqn. 7}$$

A third intensity component image $I_2$ is obtained. For example, a ¼ waveplate can be introduced into the image optical path with a $\sqrt{2}(M_{31}+iM_{32})$ pupil filter applied as above. This can be used to generate the third intensity component image $I_3$ such that:

$$I_2(\vec{x}) = \iint d^2 \vec{K}_s S(\vec{K}_s) |\iint d\vec{k} [m_{zx}(\vec{k})+im_{zy}(\vec{k})][E_x(\vec{k}, \vec{K}_s)+iE_y(\vec{k}, \vec{K}_s)] \exp[i\vec{k} \cdot \vec{x}]|^2 \quad \text{Eqn. 8}$$

A fourth intensity component image $I_3$ is also obtained by rotating the ¼ waveplate and introduce a $\sqrt{2}(M_{31}+iM_{32})$ pupil filter (applied as above). This can be used to generate the third intensity component image $I_3$ such that:

$$I_3(\vec{x}) = \iint d^2 \vec{K}_s S(\vec{K}_s) |\iint d\vec{k} [m_{zx}(\vec{k})-im_{zy}(\vec{k})][E_x(\vec{k}, \vec{K}_s)-iE_y(\vec{k}, \vec{K}_s)] \exp[i\vec{k} \cdot \vec{x}]|^2 \quad \text{Eqn. 8}$$

Additionally, similar to the unipolarized case, a fifth and sixth pair of component intensity images ($I_4$, $I_5$) can be obtain which are modeled as:

$$I_4(\vec{x}) = \iint d^2 \vec{K}_s S(\vec{K}_s) |\iint d\vec{k} [m_{zx}(\vec{k})E_x(\vec{k}, \vec{K}_s)] \exp[i\vec{k} \cdot \vec{x}]|^2 \quad \text{Eqn. 9}$$

$$I_5(\vec{x}) = \iint d^2 \vec{K}_s S(\vec{K}_s) |\iint d\vec{k} [m_{zy}(\vec{k})E_y(\vec{k}, \vec{K}_s)] \exp[i\vec{k} \cdot \vec{x}]|^2 \quad \text{Eqn. 10}$$

Thus, each one of the values, $I_0$, $I_1$, $I_2$, $I_3$, $I_4$, and $I_5$ are experimentally measured (i.e., images are taken for each one) and a composite intensity value that corrects for the high NA effects and the polarization effects is obtained. This allows a measured and modeled value of intensity.

$$E_z^{image} = I_z^{image} = I_4 + I_5 + \frac{I_0 + I_1 - I_2 - I_3}{4} \quad \text{Eqn. 11}$$

It can be shown that this is equivalent to Eqn. 6. A similar measurement can be taken for $E_x^{image}$ and $E_y^{image}$ to obtain a reconstructed image that models the mask polarization effects and the high NA effects of the lithography tool. This method enables the reconstruction of a coherent image without the need for an interferometer.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. Further, reference in the claims to an element in the singular is not intended to mean "one and only one" unless explicitly stated, but rather, "one or more". Furthermore, the embodiments illustratively disclosed herein can be practiced without any element, which is not specifically disclosed herein.

We claim:

1. A method for inspecting a surface to identify lithographically significant defects, the method comprising:
    providing a mask reticle configured to achieve photolithographic transfer of a mask pattern onto a substrate using a high numeric aperture (NA) lithography system having a high image numeric aperture (NA);
    processing the optical parameters of the high NA lithography system to obtain a plurality of matrix values associated with a high NA correction matrix that characterizes the optical parameters of the high NA lithography system;
    illuminating a portion of the mask reticle with a magnification inspection tool to produce a patterned illumination beam associated with a lithography pattern formed on the target;
    filtering the illumination beam with a one or more filters to obtain one or more filtered beams, the filters comprising values associated with the matrix values of the high NA correction matrix, so that filtered beams conform to a model of optical performance of the high NA lithography system;
    detecting the one or more filtered beams and producing raw image data associated with each filtered beam; and
    processing the raw image data associated with the filtered beams to obtain a reconstructed image.

2. The method as in claim 1 wherein processing the raw image data comprises
    summing the plurality of raw images together to obtain a reconstructed image.

3. The method as in claim 1 wherein processing further comprises
    processing the reconstructed image together with a model of photoresist characteristics to obtain a resist-modeled reconstructed image; and comparing the resist modeled reconstructed image with a reference image to conduct inspection including one of pattern verification and defect detection.

4. The method as in claim 1 further comprising:
comparing the reconstructed image with a reference to achieve at least one of defect detection or pattern verification; and wherein the reference comprises at least one of:
a data base model of an intended mask pattern after being processed to include optical proximity correction features and being processed with a lithography process model associated with the lithography system to form a simulated lithographically modeled image;
a data base model of an intended mask pattern after being processed to include optical proximity correction features and being processed with a lithography process model associated with the lithography system and further processed with a photoresist model to obtain a simulated resist-modeled image; and
a data base model of an intended mask pattern.

5. The method as in claim 4 wherein comparing the reconstructed image with a reference comprises:
obtaining the data base model of an intended mask pattern after being processed to include optical proximity correction features and being processed with a lithography process model associated with the lithography system to form a simulated lithographically modeled image; and
comparing the simulated lithographically modeled image with the reconstructed image to detect defects in the mask reticle.

6. The method as in claim 4 wherein comparing the reconstructed image with a reference comprises:
obtaining the data base model of an intended mask pattern after being processed to include optical proximity correction features and being processed with a lithography process model associated with the lithography system and being further processed with a photoresist model to obtain a simulated resist-modeled image; and
processing the reconstructed image with a photoresist model to obtain a resist-modeled reconstructed image; and
comparing the simulated resist-modeled image with the resist-modeled reconstructed image to detect defects in the mask reticle.

7. The method as in claim 4 wherein comparing the reconstructed image with a reference comprises:
obtaining the data base model of an intended mask pattern; and
processing the reconstructed image with a photoresist model to obtain a resist-modeled reconstructed image; and
comparing the data base model of an intended mask pattern with the resist modeled reconstructed image to verify that the correctness of the mask reticle.

8. The method of claim 1 wherein illuminating the mask reticle with the inspection tool includes
illuminating the mask reticle with illumination parameters that are matched to illumination optical parameters of the lithography system.

9. The method of claim 1 wherein filtering the illumination beam with a plurality of filters further includes
introducing phase correcting optical elements to produce a plurality of intensity component images that can be combined to model both the optical performance of the high NA lithography system and the polarization effects of the mask reticle.

10. A method for inspecting a surface to identify lithographically significant defects, the method comprising:
providing a mask reticle configured to achieve photolithographic transfer of a mask pattern onto a substrate using a high numeric aperture (NA) lithography system having a high image numeric aperture (NA);
illuminating a portion of the mask reticle with a magnification inspection tool to produce a patterned illumination beam associated with a lithography pattern formed on said portion of the mask reticle;
filtering the illumination beam with one or more filters to obtain one or more filtered beams, the filters enabling correction of polarization specific phase change effects induced by the magnification inspection tool and accounting for polarization specific phase change effects induced by the high NA lithography system;
capturing a plurality of raw images, each associated with the one or more filtered beams; and
processing the raw images together to obtain a reconstructed image that models high NA effects produced by the high NA lithography system.

11. The method as in claim 10 wherein the processing further comprises
processing the reconstructed image together with a model of photoresist characteristics to obtain a resist-modeled reconstructed image; and
comparing the resist modeled reconstructed image with a reference image to conduct inspection including one of pattern verification and defect detection.

12. The method as in claim 11 wherein the processing further comprises
processing the reconstructed image together with a model of etching characteristics to obtain a resist and etch modeled reconstructed image; and
comparing the resist and etch modeled reconstructed image with a reference image to conduct inspection including one of pattern verification and defect detection.

13. An inspection apparatus for reconstructing a lithographically significant pattern generated by a stepper, the apparatus comprising:
an illumination system configured to direct illumination through a mask reticle to produce a patterned illumination beam;
magnification optics for magnifying and projecting the illumination beam onto an image sensor, the magnification optics including,
a pupil plane,
a filter that models optical effects produced by a lithographic device used to print image patterns from the mask reticle, the filter located in the pupil plane and arranged to receive the beam to form a filtered beam, the filter comprising values associated with matrix values of a high NA correction matrix that characterizes optical parameters of a high NA lithography system so that the filtered beam conforms to a model of optical performance of the high NA lithography system; and
an image sensor for receiving the filtered beam and producing an output signal associated with the filtered beam.

14. An inspection apparatus for reconstructing a lithographically significant pattern generated by a stepper, the apparatus comprising:
an illumination source directed through an illumination lens system and illumination aperture onto a mask reticle to produce a patterned illumination beam;

magnification optics for magnifying and projecting the beam onto an image sensor, the magnification optics including
a first stage optical system,
a second stage optical system,
a pupil plane arranged between the first and second stages of the magnification optical system,
a third optical element arranged between the first stage optical system and the pupil plane, the third optical element configured to generate one or more optical beams,
one or more filters that model optical effects produced by a lithographic device projection optics of a stepper device used to print image patterns from the mask reticle on a substrate and are located in the pupil plane and arranged to receive at least one of the one or more optical beams to form a filtered beam and, wherein each filter corresponds to a different pupil function defined by the high NA correction matrix; and
one or more sensors, each sensor arranged to receive at least one of the one or more filtered beams to generate one or more output signals, each output signal associated with one of the plurality of filtered beams; and
processing circuitry for
receiving one or more output signals from the one or more image sensors and
processing the one or more signals from one or more filtered beams to obtain at least one reconstructed image associated with the mask reticle.

15. The inspection apparatus as recited in claim 14 wherein the circuitry for reconstructing an image associated with the mask reticle from the one or more output signals includes circuitry for
reconstructing an image associated with a mask reticle image as projected through the lithography device.

16. The inspection apparatus as recited in claim 14 wherein
the third optical element is configured to generate a pair of optic beams;
the one or more filters include a pair of filters wherein each filter is arranged to receive one of the pair of optical beams; and
the sensor comprises two sensors, each sensor of the two sensors arranged to receive one of the pair of filtered beams to generate an output signal.

17. The method of claim 1, wherein the filtering the illumination beam with a one or more filters to obtain one or more filtered beams comprises:
filtering the illumination beam with two or more filters to simultaneously obtain two or more filtered beams.

18. The method of claim 10, wherein the filtering the illumination beam with a one or more filters to obtain one or more filtered beams comprises:
filtering the illumination beam with two or more filters to simultaneously obtain two or more filtered beams.

* * * * *